US008907046B2

(12) United States Patent
Iyer et al.

(10) Patent No.: US 8,907,046 B2
(45) Date of Patent: Dec. 9, 2014

(54) COPOLYMERS WITH PERFLUOROPOLYETHER SEGMENT AND MULTIPLE AMINOOXALYLAMINO GROUPS

(75) Inventors: Suresh S. Iyer, Woodbury, MN (US); Miguel A. Guerra, Woodbury, MN (US); Richard G. Hansen, Mahtomedi, MN (US); David S. Hays, Woodbury, MN (US); Ramesh C. Kumar, Woodbury, MN (US); George G. I. Moore, Afton, MN (US); Yu Yang, Eden Prairie, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 226 days.

(21) Appl. No.: 13/514,661

(22) PCT Filed: Dec. 22, 2010

(86) PCT No.: PCT/US2010/061709
§ 371 (c)(1),
(2), (4) Date: Jun. 8, 2012

(87) PCT Pub. No.: WO2011/082046
PCT Pub. Date: Jul. 7, 2011

(65) Prior Publication Data
US 2012/0259088 A1   Oct. 11, 2012

Related U.S. Application Data

(60) Provisional application No. 61/291,083, filed on Dec. 30, 2009.

(51) Int. Cl.
*C08G 69/08* (2006.01)
*C08G 69/26* (2006.01)
*C08G 69/40* (2006.01)

(52) U.S. Cl.
CPC .............. *C08G 69/265* (2013.01); *C08G 69/40* (2013.01)
USPC ............. 528/343; 528/70; 528/244; 528/310; 528/324; 528/329.1; 528/401

(58) Field of Classification Search
USPC ......... 528/70, 244, 310, 324, 329.1, 343, 401
See application file for complete search history.

(56) References Cited

U.S. PATENT DOCUMENTS

| | | | |
|---|---|---|---|
| 2,343,808 A | 3/1944 | Schlack | |
| 3,250,807 A | 5/1966 | Fritz | |
| 3,392,097 A | 7/1968 | Gozzo | |
| 3,442,942 A | 5/1969 | Sianesi | |
| 3,485,806 A | 12/1969 | Bloomquist | |
| 3,634,362 A * | 1/1972 | Oldham | 528/336 |
| 3,699,145 A | 10/1972 | Sianesi | |
| 3,715,378 A | 2/1973 | Sianesi | |
| 3,728,311 A | 4/1973 | Park | |
| 3,810,874 A | 5/1974 | Mitsch | |
| 3,890,269 A | 6/1975 | Martin | |
| 4,085,137 A | 4/1978 | Mitsch | |
| 4,119,615 A | 10/1978 | Schulze | |
| 4,661,577 A | 4/1987 | Jo Lane | |
| 4,684,728 A | 8/1987 | Möhring | |
| 5,026,890 A | 6/1991 | Webb | |
| 5,093,432 A | 3/1992 | Bierschenk | |
| 5,214,119 A | 5/1993 | Leir | |
| 5,266,650 A | 11/1993 | Guerra | |
| 5,276,122 A | 1/1994 | Aoki | |
| 5,461,134 A | 10/1995 | Leir | |
| 5,488,142 A | 1/1996 | Fall | |
| 5,512,650 A | 4/1996 | Leir | |
| 5,663,127 A | 9/1997 | Flynn | |
| 6,313,335 B1 | 11/2001 | Roberts | |
| 6,355,759 B1 | 3/2002 | Sherman | |
| 6,511,721 B1 | 1/2003 | Murata | |
| 6,923,921 B2 | 8/2005 | Flynn | |
| 7,335,786 B1 | 2/2008 | Iyer | |
| 7,371,464 B2 | 5/2008 | Sherman | |
| 7,501,184 B2 | 3/2009 | Leir | |
| 7,745,653 B2 | 6/2010 | Iyer | |
| 7,883,652 B2 | 2/2011 | Leir | |
| 8,552,124 B2 * | 10/2013 | Hansen et al. | 525/474 |

(Continued)

FOREIGN PATENT DOCUMENTS

| | | |
|---|---|---|
| EP | 1388556 | 2/2004 |
| EP | 2096133 | 9/2009 |

(Continued)

OTHER PUBLICATIONS

De Abajo, "Carbon-13 NMR Sequence Analysis. 23. Synthesis and NMR Spectroscopic Characterization of Polyoxamides with Alternating and Random Sequences of Aliphatic Diamines", Journal of Macromolecular Science, Chemistry, 1984, vol. A21, No. 4, pp. 411-426.

Gaade, "The Interaction of Diethyl Oxalate and Ethane Diamine", Recueil des Travaux Chimiques des Pays-Bas, Jan. 25, 1936, vol. 55, pp. 325-230.

Gaade, "Esters of Ethane-1 : 2-Dioxamic Acid and Their Derivatives II", Recueil des Travaux Chimiques des Pays-Bas, Jan. 25, 1936, vol. 55, pp. 541-559.

Vogl, "Polyoxamides. I. Preparation and Characterization of Cyclic Oxamides", Macromolecules, Jul.-Aug. 1968, vol. 1, No. 4, pp. 311-315.

International Search Report for PCT/US2010/061709, 3 pages.

*Primary Examiner* — Gregory Listvoyb
(74) *Attorney, Agent, or Firm* — Jean A. Lown

(57) ABSTRACT

Copolymers containing at least one perfluoropolyether segment and multiple aminooxalylamino groups are described. Methods of making the copolymers are also described. The copolymers can be prepared by reacting an oxalylamino-containing compound and an amine compound having at least two primary amino groups, at least two secondary amino groups, or at least one primary amino group plus at least one secondary amino group.

5 Claims, No Drawings

(56) References Cited

U.S. PATENT DOCUMENTS

| | | |
|---|---|---|
| 2007/0148474 A1 | 6/2007 | Leir |
| 2007/0149745 A1 | 6/2007 | Leir |
| 2008/0318057 A1 | 12/2008 | Sherman |
| 2008/0318058 A1 | 12/2008 | Sherman |
| 2011/0092638 A1 | 4/2011 | Leir |
| 2012/0264890 A1 | 10/2012 | Hansen |
| 2012/0271025 A1 | 10/2012 | Hays |
| 2012/0289736 A1 | 11/2012 | Yang |
| 2013/0172520 A1 * | 7/2013 | Maeda et al. .......... 528/343 |

FOREIGN PATENT DOCUMENTS

| | | |
|---|---|---|
| WO | 96/34030 | 10/1996 |
| WO | 2004/034139 | 4/2004 |
| WO | 2005/003210 | 1/2005 |
| WO | 2007/073502 | 6/2007 |
| WO | 2007/075317 | 7/2007 |
| WO | 2007/075802 | 7/2007 |
| WO | 2007/082046 | 7/2007 |
| WO | 2008/027594 | 3/2008 |
| WO | 2009/002611 | 12/2008 |

* cited by examiner

COPOLYMERS WITH PERFLUOROPOLYETHER SEGMENT AND MULTIPLE AMINOOXALYLAMINO GROUPS

CROSS REFERENCE TO RELATED APPLICATIONS

This application is a national stage filing under 35 U.S.C. 371 of PCT/US2010/061709, filed Dec. 22, 2010, which claims priority to U.S. Provisional Application No. 61/291,083, filed Dec. 30, 2009, the disclosure of which is incorporated by reference in its/their entirety herein.

TECHNICAL FIELD

Copolymers containing at least one perfluoropolyether segment and multiple aminooxalylamino groups as well as methods of making these copolymers are described.

BACKGROUND

Fluorinated polymeric materials such as those containing perfluoropolyether segments have been used in applications where low surface energy materials and/or low refractive index materials are desired.

Polymeric materials with multiple aminooxalylamino groups plus polydiorganosiloxane segments have been prepared. These polymeric materials can be used, for example, to prepare adhesive compositions and various types of polymeric films.

SUMMARY

Copolymers containing at least one perfluoropolyether segment and multiple aminooxalylamino groups are described. Methods of making the copolymers are also described. The copolymers can be used, for example, in applications where low surface energy materials and/or low refractive index materials are desired.

In a first aspect, a copolymer is provided. The copolymer includes a product of a reaction mixture that includes a fluorinated oxalylamino-containing compound and a first amine compound. The fluorinated oxalylamino-containing compound includes a perfluoropolyether segment and at least two monovalent oxalylamino-containing groups of Formula (I).

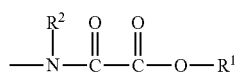

In Formula (I), each $R^1$ is independently an alkyl, haloalkyl, aralkyl, substituted aralkyl, alkenyl, aryl, substituted aryl, or imino of formula $-N=CR^4R^5$. Each $R^2$ is independently hydrogen, alkyl, aralkyl, or aryl. Group $R^4$ is hydrogen, alkyl, aralkyl, substituted aralkyl, aryl, or substituted aryl. Group $R^5$ is an alkyl, aralkyl, substituted aralkyl, aryl, or substituted aryl. The first amine compound is of Formula (II).

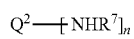

In Formula (II), group $Q^2$ is (a) an alkane radical, (b) a fluorinated alkane radical, (c) a heteroalkane radical, (d) an arene radical, (e) a carbonylamino group linking a first group to a second group, where each first group and second group is independently an alkane radical, a fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each group $R^7$ is independently hydrogen, alkyl, aralkyl, aryl, or part of a heterocyclic group that includes $Q^2$ and the nitrogen to which $R^7$ is attached. The variable n is an integer equal to at least 2.

In a second aspect, a copolymer is provided. The copolymer includes a product of a second oxalylamino-containing compound and a fluorinated amine. The second oxalylamino-containing compound is of Formula (III).

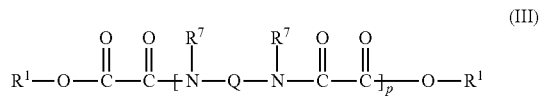

In Formula (III), each $R^1$ is independently an alkyl, haloalkyl, aralkyl, substituted aralkyl, alkenyl, aryl, substituted aryl, or imino of formula $-N=CR^4R^5$. Each $R^7$ is independently hydrogen, alkyl, aralkyl, aryl, or part of a heterocyclic group that includes Q and a nitrogen to which $R^7$ is attached. Group $R^4$ is hydrogen, alkyl, aralkyl, substituted aralkyl, aryl, or substituted aryl. Group $R^5$ is alkyl, aralkyl, substituted aralkyl, aryl, or substituted aryl. Group Q is (a) an alkylene, (b) fluorinated alkylene, (c) heteroalkylene, (d) arylene, (e) a carbonylamino group linking a first group to a second group, wherein the first group and the second group are each independently an alkylene, fluorinated alkylene, heteroalkylene, arylene, a combination thereof, (f) part of a heterocyclic group that includes $R^7$ and the nitrogen to which $R^7$ is attached, or (g) a combination thereof. The variable p is an integer equal to at least 1. The fluorinated amine contains a perfluoropolyether segment and at least two primary amino groups, at least two secondary amino groups, or at least one primary amino group plus at least one secondary amino group.

In a third aspect, a copolymer is provided. The copolymer includes a product of a reaction mixture that includes an oxalate compound, a fluorinated amine compound, and a first amine compound. The oxalate compound is of Formula (IX).

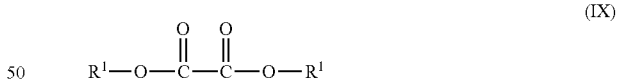

In Formula (IX), each $R^1$ is independently an alkyl, haloalkyl, aralkyl, substituted aralkyl, alkenyl, aryl, substituted aryl, or imino of formula $-N=CR^4R^5$. Group $R^4$ is hydrogen, alkyl, aralkyl, substituted aralkyl, aryl, or substituted aryl. Group $R^5$ is alkyl, aralkyl, substituted aralkyl, aryl, or substituted aryl. The fluorinated amine contains a perfluoropolyether segment and at least two primary amino groups, at least two secondary amino groups, or at least one primary amino group plus at least one secondary amino group. The first amine compound is of Formula (II).

In Formula (II), group $Q^2$ is (a) an alkane radical, (b) a fluorinated alkane radical, (c) a heteroalkane radical, (d) an arene radical, (e) a carbonylamino group linking a first group to a second group, where each first group and second group is independently an alkane radical, a fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each group $R^7$ is independently hydrogen, alkyl, aralkyl, aryl, or part of a heterocyclic group that includes $Q^2$ and the nitrogen to which $R^7$ is attached. The variable n is an integer equal to at least 2.

In a fourth aspect, a copolymer is provided. The copolymer contains at least one group of Formula (IV).

$$*-\left[\left[\begin{array}{cccc} R^2 & R^2 & O & O \\ | & | & || & || \\ N-Q^1-N-C-C \end{array}\right]_q \left[\begin{array}{cccc} R^7 & R^7 & O & O \\ | & | & || & || \\ N-Q-N-C-C \end{array}\right]_p\right]_m-* \quad (IV)$$

In Formula (IV), each group $Q^1$ contains a perfluoropolyether segment. Each group Q is (a) an alkylene, (b) fluorinated alkylene, (c) heteroalkylene, (d) arylene, (e) a carbonylamino group linking a first group to a second group, wherein the first group and the second group are each independently an alkylene, fluorinated alkylene, heteroalkylene, arylene, a combination thereof, (f) part of a heterocyclic group that includes $R^7$ and a nitrogen to which $R^7$ is attached, or (g) a combination thereof. Each $R^2$ is independently hydrogen, alkyl, aralkyl, or aryl. Each $R^7$ is independently hydrogen, alkyl, aralkyl, aryl, or part of a heterocyclic group that includes Q and a nitrogen to which $R^7$ is attached. Each variable q, p, and m is an integer equal to at least 1. Each asterisk denotes a site of attachment to another group in the copolymer.

The above summary is not intended to describe each disclosed embodiment or every implementation of the present invention. The description that follows more particularly exemplifies illustrative embodiments. In several places through the description, guidance is provided through lists of examples, which can be used in various combinations. In each instance, unless stated to the contrary, the recited list serves only as a representative group and should not be interpreted as an exclusive list.

DETAILED DESCRIPTION

Copolymers containing perfluoropolyether segments are described. The copolymers further include at least two aminooxalylamino groups. Methods of making the copolymers are also described.

DEFINITIONS

The terms "a", "an", and "the" are used interchangeably with "at least one" to mean one or more of the elements being described.

The term "and/or" means either or both. For example, the expression X and/or Y means X, Y, or a combination thereof.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, ethylhexyl, and octadecyl.

The term "alkylene" refers to a divalent group that is a radical of an alkane. The alkylene can be straight-chained, branched, cyclic, or combinations thereof. The alkylene typically has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "fluorinated alkylene" refers to an alkylene having at least one hydrogen atom replaced with a fluorine atom. Perfluoroalkylenes are a subset of fluorinated alkylenes.

The term "alkoxy" refers to a monovalent group of formula —OR where R is an alkyl group.

The term "alkoxycarbonyl" refers to a monovalent group of formula —(CO)OR where (CO) denotes a carbonyl group and R is an alkyl group.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 6, or 2 to 4 carbon atoms. Exemplary alkenyl groups include ethenyl, 1-propenyl, and 1-butenyl.

The term "arene" refers to a carbocyclic aromatic compound.

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, naphthyl, acenaphthyl, anthraquinonyl, phenanthryl, anthracenyl, pyrenyl, perylenyl, and fluorenyl.

The term "substituted aryl" refers to an aryl substituted with one or more groups selected from halo, alkyl, haloalkyl, alkoxy, or alkoxycarbonyl.

The term "aralkyl" refers to a monovalent group of formula —R—Ar where R is an alkylene and Ar is an aryl group. That is, the aralkyl is an alkyl substituted with an aryl.

The term "substituted aralkyl" refers to an aralkyl substituted with one or more groups selected from halo, alkyl, haloalkyl, alkoxy, or alkoxycarbonyl. The aryl portion of the aralkyl is typically the group that is substituted.

The term "aralkylene" refers to a divalent group of formula —R—$Ar^a$— where R is an alkylene and $Ar^a$ is an arylene group.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "halocarbonyl" refers to a monovalent group of formula —(CO)X where (CO) denotes a carbonyl and X is halo.

As used herein, the term "imino" refers to a group of formula —N=$CR^4R^5$ where the $R^4$ group is hydrogen, alkyl, aralkyl, substituted aralkyl, aryl, or substituted aryl and the $R^5$ group is alkyl, aralkyl, substituted aralkyl, aryl, or substituted aryl.

The term "heteroalkylene" refers to a divalent group that includes at least two alkylene groups connected by a thio, oxy, or —$NR^2$— where $R^2$ is hydrogen, alkyl, aryl, or aralkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms. Some heteroalkylene groups are polyalkylene oxide groups where the heteroatoms are oxygen.

The term "perfluoropolyether" refers to divalent group or segment of formula $-(C_xF_{2x}-O)_y-$ where x is an integer in the range of 1 to 10 and y is an integer equal to at least 2. The integer x is often in the range of 1 to 8, in the range of 1 to 6, in the range of 1 to 4, in the range of 2 to 4, equal to 3, or equal to 4. The integer y is often at least 3, at least 4, at least 8, at least 12, at least 16, at least 20, at least 30, at least 40, or at least 50.

The term "perfluoroalkylene" refers to an alkylene in which all of the hydrogen atoms are replaced with fluorine atoms.

The term "oxalyl" refers to a divalent group of formula —(CO)—(CO)— where each (CO) denotes a carbonyl group.

The term "oxalylamino" refers to a divalent group of formula —(CO)—(CO)—$NR^a$— where each (CO) denotes a carbonyl group and where $R^a$ is hydrogen, alkyl, aryl, aralkyl, or part of a heterocyclic group.

The term "aminooxalylamino" refers to a divalent group of formula —$NR^a$—(CO)—(CO)—$NR^a$— where each (CO) denotes a carbonyl group and each $R^a$ is hydrogen, alkyl, aryl, aralkyl, or part of a heterocyclic group.

The term "carbonylamino" refers to a divalent group of formula —(CO)—$NR^a$— where each (CO) denotes a carbonyl group and where $R^a$ is hydrogen, alkyl, aryl, aralkyl, or part of a heterocyclic group.

The term "primary amino" refers to a monovalent group —$NH_2$.

The term "secondary amino" refers to a monovalent group —$NHR^3$ where $R^3$ is an alkyl, aryl, aralkyl, or part of a heterocyclic group.

The terms "polymer" and "polymeric material" are used interchangeably and refer to materials prepared from one or more reactants (i.e., monomers). Likewise, the term "polymerize" refers to the process of making a polymeric material from one or more reactants. The terms "copolymer" and "copolymer" are used interchangeably and refer to polymeric material prepared from at least two different reactants.

Various copolymers are provided that include at least one perfluoropolyether segment and at least two aminooxalylamino groups. These copolymers include a product of a first reaction mixture that includes a fluorinated oxalylamino-containing compound and first amine compound. The fluorinated oxalylamino-containing compound has a perfluoropolyether segment. Alternatively, the copolymers include a product of a second reaction mixture that includes a second oxalylamino-containing compound and a fluorinated amine having a perfluoropolyether segment. The fluorinated oxalylamino-containing compound in the first reaction mixture and the second oxalylamino-containing compound in the second reaction mixture each have at least two monovalent oxalylamino-containing groups of Formula (I).

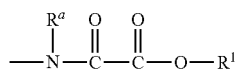

(I)

In Formula (I), each $R^1$ is independently an alkyl, haloalkyl, aralkyl, substituted aralkyl, alkenyl, aryl, substituted aryl, or imino of formula —N=$CR^4R^5$. Each $R^a$ is independently hydrogen, alkyl, aralkyl, aryl, or part of a heterocyclic group that includes a nitrogen to which $R^a$ is attached. Group $R^4$ group is hydrogen, alkyl, aralkyl, substituted aralkyl, aryl, or substituted aryl. Group $R^5$ is alkyl, aralkyl, substituted aralkyl, aryl, or substituted aryl.

In the first reaction mixture used to form the copolymer, the compound having at least two oxalylamino-containing groups of Formula (I) is a fluorinated compound having a perfluoropolyether segment. In this reaction mixture, the oxalylamino-containing group is of Formula (Ia).

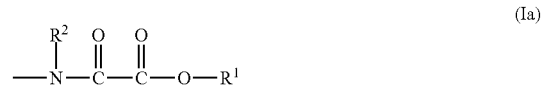

(Ia)

In Formula (Ia), group $R^2$ is hydrogen, alkyl, aralkyl, or aryl.

In some embodiments, the fluorinated oxalylamino-containing compound is of Formula (V).

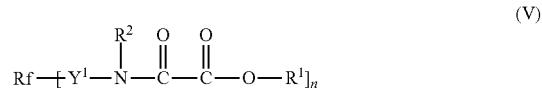

(V)

In Formula (V), Rf is a perfluoropolyether group. Each $Y^1$ is independently a) a heteroalkylene, (b) alkylene, or (c) a carbonylamino group linking a first group to a second group, wherein each first group and second group is independently a heteroalkylene or alkylene, or (d) a combination thereof. The variable n is an integer greater than or equal to at least 2. For example, n can be at least 3 or at least 4. The variable n is often no greater than 10, no greater than 8, no greater than 6, no greater than 4, or no greater than 3. The variable n can be in the range of 2 to 10, 2 to 6, or 2 to 4. The valency of Rf is equal to n. To prepare a linear reaction product, n is usually equal to 2 and Rf is a divalent group.

Suitable alkyl and haloalkyl groups for $R^1$ in Formulas (I), (Ia), and (V) often have 1 to 10, 1 to 6, or 1 to 4 carbon atoms. Although tertiary alkyl (e.g., tert-butyl) and tertiary haloalkyl groups can be used, a primary or secondary carbon atom is often attached directly (i.e., bonded) to the adjacent oxy group. Exemplary alkyl groups include methyl, ethyl, n-propyl, iso-propyl, n-butyl, and iso-butyl. Exemplary haloalkyl groups include chloroalkyl groups and fluoroalkyl groups in which some, but not all, of the hydrogen atoms on the corresponding alkyl group are replaced with halo atoms. For example, the chloroalkyl or fluoroalkyl groups can be chloromethyl, 2-chloroethyl, 2,2,2-trichloroethyl, 3-chloropropyl, 4-chlorobutyl, fluoromethyl, 2-fluoroethyl, 2,2,-difluoroethyl, 2,2,2-trifluoroethyl, 1-(trifluoromethyl)-2,2,2-trifluoroethyl, 3-fluoropropyl, 4-fluorobutyl, and the like.

Suitable alkenyl groups for $R^1$ often have 2 to 10, 2 to 8, 2 to 6, or 2 to 4 carbon atoms. Exemplary alkenyl groups include ethenyl, propenyl, butenyl, and pentenyl.

Suitable aryl groups for $R^1$ include those having 6 to 12 carbon atoms such as, for example, phenyl. The aryl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable aralkyl groups for $R^1$ include those having an alkyl group with 1 to 10 carbon atoms and an aryl group with 6 to 12 carbon atoms. For example, the aralkyl can be an alkyl having 1 to 10 carbon atoms or 1 to 4 carbon atoms substituted with phenyl. The aryl portion of the aralkyl can be unsubstituted or substituted with an alkyl (e.g., an alkyl having 1 to 4 carbon atoms such as methyl, ethyl, or n-propyl), an alkoxy (e.g., an alkoxy having 1 to 4 carbon atoms such as methoxy, ethoxy, or propoxy), halo (e.g., chloro, bromo, or fluoro), a haloalkyl (e.g., a haloalkyl having 1 to 4 carbon atoms such as trifluoromethyl), or alkoxycarbonyl (e.g., an alkoxycarbonyl having 2 to 5 carbon atoms such as methoxycarbonyl, ethoxycarbonyl, or propoxycarbonyl).

Suitable imino groups for $R^1$ are monovalent groups of formula $-N=CR^4R^5$. Suitable alkyl groups for either $R^4$ or $R^5$ can be linear or branched and typically contain 1 to 10 carbon atoms, 1 to 8 carbon atoms, 1 to 6 carbon atoms, or 1 to 4 carbon atoms. Suitable aryl, substituted aryl, aralkyl, and substituted aralkyl groups for $R^4$ or $R^5$ are the same as those describe above for $R^1$.

Each $R^2$ group in Formula (Ia) and (V) can be independently hydrogen, alkyl, aralkyl, or aryl. Suitable alkyl groups can be linear or branched and typically contain 1 to 10 carbon atoms, 1 to 8 carbon atoms, 1 to 6 carbon atoms, or 1 to 4 carbon atoms. Suitable aryl groups typically include those having 6 to 12 carbon atoms. The aryl group is often phenyl. Suitable aralkyl groups include those having an alkyl group with 1 to 10 carbon atoms substituted with an aryl group having 6 to 12 carbon atoms. Exemplary aralkyl groups often include an alkyl having 1 to 10 carbon atoms or 1 to 4 carbon atoms substituted with a phenyl.

The group Rf in Formula (V) is a perfluoropolyether group. This group typically includes a segment of formula $-(C_xF_{2x}-O)_y-$ where x is an integer in the range of 1 to 10 and y is an integer equal to at least 2. The integer x is often in the range of 1 to 8, in the range of 1 to 6, in the range of 1 to 4, in the range of 2 to 4, equal to 3, or equal to 4. The integer y is often at least 3, at least 4, at least 8, at least 12, at least 16, at least 20, at least 30, at least 40, or at least 50. In some specific perfluoropolyether groups, x is equal to 3 and the perfluoropolyether group includes a poly(hexafluoropropylene oxide) segment. That is, Rf often includes a segment of formula $-(C_3F_6O)_y-$ and each $-C_3F_6O-$ group in the segment can be linear or branched. The valency of the Rf group is equal to the variable n. In many embodiments, Rf is a divalent group.

Some exemplary Rf groups are of formula

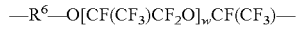

where $R^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variable w is an integer in the range of 1 to 35, in the range of 1 to 30, in the range of 1 to 20, in the range of 1 to 10, or in the range of 1 to 5.

Other exemplary Rf groups are of formula

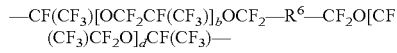

where $R^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variables b and d are both integers with a sum in the range of 0 to 35, in the range of 1 to 35, in the range of 2 to 35, in the range of 0 to 30, in the range of 1 to 30, in the range of 2 to 30, in the range of 0 to 20, in the range of 1 to 20, in the range of 2 to 20, in the range of 0 to 10, in the range of 1 to 20, or in the range of 2 to 10. The preparation of the corresponding dimethyl esters of these Rf groups is described, for example, in U.S. Pat. No. 3,250,807 (Fritz et al.) such as Example IV of that patent.

Yet other exemplary Rf groups are of formula

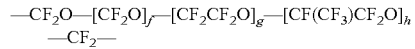

where the variables f, g, and h are integers with a sum in the range of 0 to 35, in the range of 1 to 35, in the range of 2 to 35, in the range of 3 to 35, in the range of 3 to 30, in the range of 3 to 20, in the range of 3 to 15, or in the range of 3 to 10. Exemplary materials are commercially available from Solvay Solexis (West Deptford, N.J.) under the trade designation FOMBLIN Z-DEAL.

Still other exemplary Rf groups are of one of the following formulas

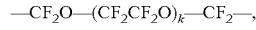

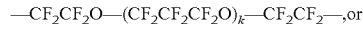

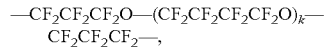

where k is a variable in the range of 0 to 35, in the range of 1 to 30, in the range of 1 to 30, in the range of 1 to 20, in the range of 1 to 15, or in the range of 1 to 10. The corresponding dimethyl esters of these Rf groups can be prepared by direct fluorination of an organic precursor that is then reacted with methanol. This preparation method is described in U.S. Pat. No. 5,488,142 (Fall et al.) such as Example 2 of that patent and in U.S. Pat. No. 5,093,432 (Bierschenk et al.) such as in Example 4 of that patent.

Each $Y^1$ in Formula (V) is independently (a) a heteroalkylene, (b) an alkylene, (c) a carbonylamino linking a first group to a second group, wherein the first group and the second group are each independently an alkylene or heteroalkylene, or (d) a combination thereof. When group $Y^1$ includes a carbonylamino group linking a first group to a second group, the resulting linked group can be of formula $-Y^{1a}-(CO)-NR^2-Y^{1a}-$ where each $Y^{1a}$ is independently an alkylene or heteroalkylene. Multiple such groups can be linked together such as, for example, $-Y^{1a}-(CO)NR^2-Y^{1a}-(CO)NR^2-Y^{1a}-$ and $-Y^{1a}-(CO)NR^2-Y^{1a}-(CO)NR^2-Y^{1a}-(CO)NR^2-Y^{1a}-$.

Although any suitable heteroalkylene group can be used for $Y^1$ (or $Y^{1a}$), the heteroalkylene often contains oxygen heteroatoms (i.e., oxy groups). The heteroalkylene often has at least 2 carbon atoms and at least one heteroatom, at least 4 carbon atoms and at least one heteroatom, at least 6 carbon atoms and at least one heteroatoms, at least 10 carbon atoms and at least 2 heteroatoms, or at least 20 carbon atoms and at least 3 or at least 4 heteroatoms. Any suitable alkylene group can be used for $Y^1$ (or $Y^{1a}$). The alkylene group can have at least 1 carbon atoms, at least 2 carbon atoms, at least 3 carbon atoms, at least 4 carbon atoms, at least 6 carbon atoms, at least 10 carbon atoms, or at least 20 carbon atoms.

In other embodiments of the first reaction mixture, the fluorinated oxalylamino-containing compound is of Formula (VI).

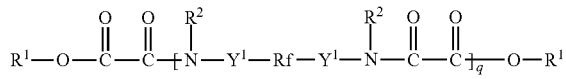

(VI)

In Formula (VI), each Rf, $Y^1$, $R^1$, and $R^2$ are the same as describe above for Formula (V). The variable q is an integer equal to at least 1 and is often equal to at least 2, at least 3, or at least 5. The variable q is often no greater than 100, no greater than 50, no greater than 20, no greater than 15, or no greater than 10. The variable q is often in the range of 1 to 20, in the range of 2 to 20, in the range of 1 to 15, in the range of 1 to 10, in the range of 1 to 6, in the range of 1 to 4, or in the range of 1 to 3. The value of q is affected by the ratio (based on equivalents) of the components reacted to form the compound of Formula (VI).

When the fluorinated oxalylamino-containing compound is of Formula (VI), there can be a mixture of materials having different values for the variable q. For example, at least 50 weight percent of the reaction product can has the variable q equal to 1 with the remainder of the reaction product having the variable q in the range of 2 to 20, in the range of 2 to 10, or in the range of 2 to 5. In some examples, at least 60 weight percent, at least 70 weight percent, at least 80 weight percent, at least 90 weight percent, or at least 95 weight percent of the reaction product has the variable q equal to 1 with the remainder of the reaction product having the variable q in the range of 2 to 20, in the range of 2 to 10, or in the range of 2 to 5.

In some fluorinated oxalylamino-containing compounds of Formula (V) or (VI), each group $Y^1$ is equal to —$Y^2$—(CO)—$NR^2$—$Y^3$— and the compounds are of Formula (Va) and (VIa), respectively.

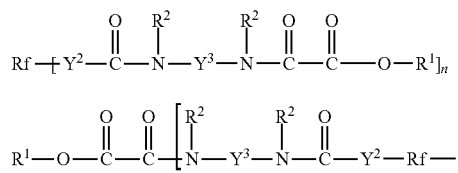

In these formulas, each $Y^2$ is independently a single bond, heteroalkylene, alkylene, or combination thereof. Each $Y^3$ is independently a heteroalkylene, alkylene, or combination thereof.

Although any suitable heteroalkylene can be used for either $Y^2$ or $Y^3$, the heteroalkylene often has oxygen heteroatoms. Each heteroalkylene includes at least 2 carbon atoms and at least one heteroatom, at least 4 carbon atoms and at least one heteroatom, at least 6 carbon atoms and at least 1 heteroatom, at least 10 carbon atoms and at least 2 heteroatoms, or at least 20 carbon atoms and at least 3 or at least 4 heteroatoms.

Suitable alkylene groups for $Y^2$ have at least one carbon atom while suitable alkylene groups for $Y^3$ have at least two carbon atoms. Exemplary alkylene groups for either $Y^2$ or $Y^3$ can have at least 2 carbon atoms, at least 4 carbon atoms, at least 6 carbon atoms, at least 10 carbon atoms, or at least 20 carbon atoms.

Some more particular fluorinated oxalylamino-containing compounds of Formula (V), (Va), (VI), or (VIa) include a Rf group of formula

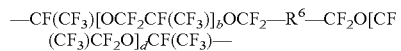

where $R^6$ is a perfluoroalkylene group having 1 to 20 carbon atoms, 1 to 10 carbon atoms, 1 to 8 carbon atoms, 1 to 6 carbon atoms, 1 to 5 carbon atoms, or 1 to 4 carbon atoms. The variables b and d are both integers with a sum in the range of 0 to 35, in the range of 1 to 35, in the range of 2 to 35, in the range of 0 to 30, in the range of 1 to 30, in the range of 2 to 30, in the range of 0 to 20, in the range of 1 to 20, in the range of 2 to 20, in the range of 0 to 10, in the range of 1 to 20, or in the range of 2 to 10. In some exemplary Rf groups, $R^6$ has 2 to 6 carbon atoms and the sum of b and d is in the range of 4 to 35.

The fluorinated oxalylamino-containing compounds of Formula (V), (Va), (VI), and (VIa) can be prepared by the reaction of a fluorinated amine with an oxalate compound. The fluorinated amine has at least one perfluoropolyether segment and at least two primary amino groups, at least two secondary amino groups, or at least one primary amino group plus at least one secondary amino group. The fluorinated amine is often of Formula (VII) or (VIII).

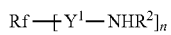

(VII)

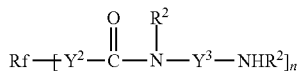

(VIII)

The compounds of Formula (VII) are the equal to those of Formula (VIII) where $Y^1$ in Formula (VII) is equal to —$Y^2$—(CO)—$NR^2$—$Y^3$—. The groups Rf, $Y^1$, $Y^2$, $Y^3$, and $R^2$ in Formulas (VII) and (VIII) are the same as previously described for Formulas (V) and (IV). The variable n is the same as previously described but is often equal to 2 as shown in Formulas (VIIa) and (VIIIa).

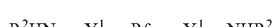

(VIIa)

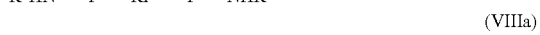

(VIIIa)

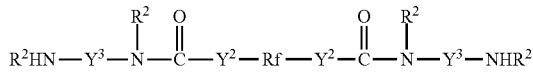

The various fluorinated amines can be prepared using any known method. For example, the fluorinated amines can be prepared by forming a compound of formula A-Rf-A. In this formula, group A refers to a carbonyl-containing group such as an alkoxycarbonyl or halocarbonyl. The preparation of such compounds is further described, for example, in U.S. Pat. No. 3,250,807 (Fritz et al.) where an initiating fluorinated diacid such as perfluorosuccinyl fluoride is reacted with hexafluoropropylene oxide in bis(2-methoxyethyl)ether (i.e., diglyme) with a catalytic amount of potassium fluoride. This compound A-Rf-A can then be reacted with a diamine of formula $R^2HN$—$Y^3$—$NHR^2$ to prepare the fluorinated amines of Formula (VIIIa) with $Y^2$ being a single bond.

Some exemplary fluorinated amines of Formula (VIIa) include, but are not limited to, those of formula Rf—(CH$_2$OC$_3$H$_6$NH$_2$)$_2$ or Rf—(CH$_2$OC$_2$H$_4$NH$_2$)$_2$ where Y$^1$ is a heteroalkylene. Other exemplary fluorinated amines include, but are not limited to, those of formula Rf—(CH$_2$CH$_2$NH$_2$)$_2$ or Rf—(CH$_2$NH$_2$)$_2$ where Y$^1$ is an alkylene.

To prepare a compound of formula Rf—(CH$_2$OC$_3$H$_6$NH$_2$)$_2$, a compound of formula Rf—(COF)$_2$ can be reduced to Rf—(CH$_2$OH)$_2$. Acrylonitrile can then be added to the compound of formula Rf—(CH$_2$OH)$_2$ to give a compound of formula Rf—(CH$_2$OC$_2$H$_4$CN)$_2$. Rf—(CH$_2$OC$_2$H$_4$CN)$_2$ can then be reduced with hydrogen in the presence of ammonia and a platinum catalyst to form a compound of formula Rf—(CH$_2$OC$_3$H$_6$NH$_2$)$_2$.

To prepare a compound of formula Rf—(CH$_2$OC$_2$H$_4$NH$_2$)$_2$, a compound of formula Rf—(COF)$_2$ can be reduced to Rf—(CH$_2$OH)$_2$. The compound Rf—(CH$_2$OH)$_2$ can then be reacted with ethylene carbonate to form a compound of formula Rf—(CH$_2$OC$_2$H$_4$OH)$_2$. This compound can then be reacted with methanesulfonyl chloride to form a compound of formula Rf—(CH$_2$OC$_2$H$_4$OSO$_2$CH$_3$)$_2$. The compound Rf—(CH$_2$OC$_2$H$_4$OSO$_2$CH$_3$)$_2$ can be reacted with liquid ammonia to form Rf—(CH$_2$OC$_2$H$_4$NH$_2$)$_2$.

To prepare a compound of formula Rf—(C$_2$H$_4$NH$_2$)$_2$, a compound of formula Rf—(COF)$_2$ can be reacted with lithium iodide to form Rf—(I)$_2$. The compound Rf—(I)$_2$ can then be reacted with ethylene to form Rf—(C$_2$H$_4$I)$_2$. This product can be further reacted with liquid ammonia to form Rf—(C$_2$H$_4$NH$_2$)$_2$.

To prepare a compound of formula Rf—(CH$_2$NH$_2$)$_2$, a compound of formula Rf—(COF)$_2$ can be reacted with ammonia to form Rf—(CONH$_2$)$_2$ and then reduced with BH$_3$ to Rf—(CH$_2$NH$_2$)$_2$. An alternative synthesis method is described in Example XIV of U.S. Pat. No. 3,810,874 (Mitsch et al.).

The oxalate that is reacted with the fluorinated amine (e.g., a compound of Formula (VII), (VIIa), (VIII), or (VIIIa)) is often a compound of Formula (IX).

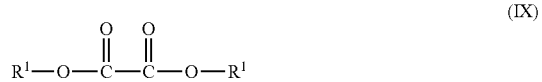

(IX)

Group R$^1$ in Formula (IX) is the same as described for Formula (I). The oxalate compound of Formula (IX) can be prepared, for example, by reacting an alcohol of formula R$^1$—OH with oxalyl chloride. Some oxalates of Formula (I) are commercially available (e.g., from Sigma-Aldrich, Milwaukee, Wis. and from VWR International, Bristol, Conn.) and include, but are not limited to, dimethyl oxalate, diethyl oxalate, di-n-butyl oxalate, di-tert-butyl oxalate, bis(phenyl) oxalate, bis(pentafluorophenyl) oxalate, 1-(2,6-difluorophenyl)-2-(2,3,4,5,6-pentachlorophenyl) oxalate, and bis(2,4,6-trichlorophenyl) oxalate.

An exemplary condensation reaction that can be used to prepare the fluorinated oxalylamino-containing compound is shown in Reaction Scheme A. More particularly, this reaction scheme shows the exemplary condensation reaction of the fluorinated amine of Formula (VIIa) with an excess of the oxalate compound of Formula (IX) is shown in Reaction Scheme A.

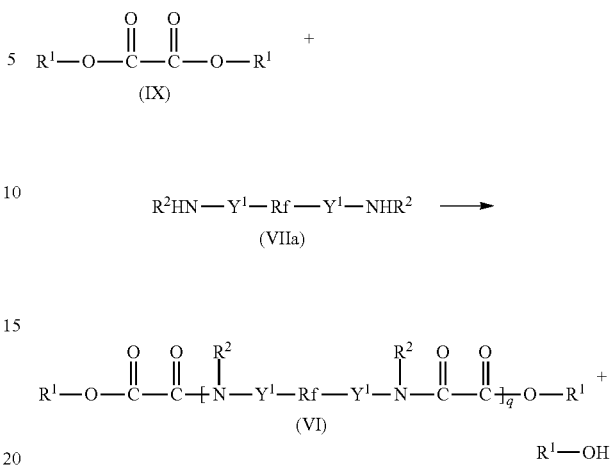

The condensation reaction between the oxalate compound of Formula (IX) and the fluorinated amine to produce a fluorinated oxalylamino-containing compound of Formula (VI) can occur in the presence or in the absence of a solvent. In some synthesis methods, no solvent or only a small amount of solvent is included in the reaction mixture. The absence of a solvent can be desirable when the removal of the solvent would be advantageous for the subsequent use of the product of the condensation reaction. In other synthesis methods, a solvent may be included such as, for example, toluene, tetrahydrofuran, dichloromethane, or aliphatic hydrocarbons (e.g., alkanes such as hexane).

An excess (e.g., an excess based on equivalents) of the oxalate compound of Formula (IX) is typically used to form the fluorinated oxalylamino-containing compound. The excess oxalate compound can typically be removed from the desired reaction product of the condensation reaction (i.e., compounds of Formulas (V), (Va), (VI), or (VIa)) using a stripping process. For example, the reacted mixture (i.e., the product or products of the condensation reaction) can be heated to a temperature up to 150° C., up to 175° C., up to 200° C., up to 225° C., or up to 250° C. or even higher to volatilize the excess oxalate. A vacuum can be pulled to lower the temperature that is needed for removal of the excess oxalate. The compounds of Formula (V), (Va), (VI), or (VIa) typically undergo minimal or no apparent degradation at temperatures up to 250° C. Any other known methods for removing the oxalate can be used.

The by-product of the condensation reaction is a compound of formula R$^1$—OH. This compound is typically an alcohol, phenol, or oxime. Group R$^1$ is often selected to produce a by-product that can be removed (e.g., vaporized) by heating at temperatures no greater than about 250° C. Such a by-product can be removed when the reacted mixture is heated to remove any excess oxalate compound of Formula (IX).

The fluorinated oxalylamino-containing compound (e.g., a compound of Formula (V), (Va), (VI), or (VIa)) can react with a first amine compound having at least two primary amino groups, at least two secondary amino groups, or at least one primary amino group plus at least one secondary amino group. The first amine compound does not have a perfluoropolyether segment. Further, the first amine compound does not have a polydiorganosiloxane segment. The first amine compound is of Formula (II).

(II)

In Formula (II), group $Q^2$ is (a) an alkane radical, (b) a fluorinated alkane radical, (c) a heteroalkane radical, (d) an arene radical, (e) a carbonylamino group linking a first group to a second group, where each first group and second group is independently an alkane radical, fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each group $R^7$ is independently hydrogen, alkyl, aralkyl, aryl, or part of a heterocyclic group that includes $Q^2$ and the nitrogen to which $R^7$ is attached. The variable n is an integer equal to at least 2.

In some embodiments, the variable n in Formula (II) is an integer equal to at least 3. When the first amine has more than three primary amino groups and/or secondary amino groups, the first amine can serve as a crosslinking agent. Examples of first amine compounds having at least three amino groups include, but are not limited to, tris(2-aminoethyl)amine, diethylene triamine, triethylene tetramine, tetraethylene pentamine, and hexaethylene heptamine.

In many embodiments of the first compound of Formula (II), the variable n is equal to two and the first compound is of Formula (IIa).

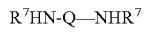
(IIa)

In Formula (IIa), the group Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^2$ is attached, or (g) a combination thereof. Each $R^7$ is independently hydrogen, alkyl, aralkyl, aryl, or part of a heterocyclic group that includes Q and the nitrogen atom to which $R^7$ is attached.

When group Q includes a carbonylamino group, the resulting linked group can be of formula -$Q^a$-(CO)NR$^7$-$Q^a$- where each $Q^a$ is independently an alkylene, fluorinated alkylene, heteroalkylene, arylene, or combination thereof. Multiple such groups can be linked such as, for example, -$Q^a$-(CO)NR$^7$-$Q^a$-(CO)NR$^7$-$Q^a$- and -$Q^a$-(CO)NR$^7$-$Q^a$-(CO)NR$^7$-$Q^a$-(CO)NR$^7$-$Q^a$-. Each $R^7$ is independently hydrogen, alkyl, aralkyl, aryl, or part of a heterocyclic group that includes $Q^a$ and the nitrogen atom to which $R^7$ is attached.

A combination in group Q or $Q^a$ refers to any combination of heteroalkylene, alkylene, fluorinated alkylene, and arylene groups. Two or more such groups can be connected. For example, the combination can be an alkylene bonded to an arylene group. Such a combination is also referred to as an aralkylene group. Another example is two or more alkylene groups bonded to an arylene group. Some exemplary groups are alkylene-aralkylene groups (i.e., alkylene-arylene-alkylene groups) of formula —$C_xH_{2x}$—$C_6H_4$—$C_xH_{2x}$— where x is in the range of 1 to 10.

Although any suitable heteroalkylene can be used for either Q or $Q^a$, the heteroalkylene often has oxygen heteroatoms. Each heteroalkylene includes at least 2 carbon atoms and at least one heteroatom, at least 4 carbon atoms and at least one heteroatom, at least 6 carbon atoms and at least 1 heteroatom, at least 10 carbon atoms and at least 2 heteroatoms, or at least 20 carbon atoms and at least 3 or at least 4 heteroatoms.

Any suitable alkylene group or fluorinated alkylene group can be used for either Q or $Q^a$. For example, the alkylene group can have at least 2 carbon atoms, at least 4 carbon atoms, at least 6 carbon atoms, at least 10 carbon atoms, or at least 20 carbon atoms. The alkylene or fluorinated alkylene groups can have, for example, 1 to 20 carbon atoms, 2 to 20 carbon atoms, 1 to 10 carbon atoms, 2 to 10 carbon atoms, 2 to 8 carbon atoms, or 2 to 6 carbon atoms. The fluorinated alkylene groups can be fully fluorinated (i.e., perfluoroalkylene groups with all of the hydrogen atoms on the alkylene replaced with fluorine atoms) or partially fluorinated (e.g., fluorinated alkylene groups with some but not all of the hydrogen atoms replaced with fluorine atoms).

Any suitable arylene can be used for Q or $Q^a$. Exemplary arylene groups often have 6 to 12 carbon atoms and include, but are not limited to, phenylene and biphenylene. The arylene group can be unsubstituted or substituted with one or more groups selected from halo, alkyl, haloalkyl, alkoxy, or alkoxycarbonyl.

Each $R^7$ group in Formula (II) or (IIa) is independently hydrogen, alkyl, aralkyl, aryl, or part of a heterocyclic group that includes Q and the nitrogen atom to which $R^7$ is attached. Suitable alkyl groups can be linear or branched and typically contain 1 to 10 carbon atoms, 1 to 8 carbon atoms, 1 to 6 carbon atoms, or 1 to 4 carbon atoms. Suitable aryl groups typically include those having 6 to 12 carbon atoms. The aryl group is often phenyl. Suitable aralkyl groups include those having an alkyl group with 1 to 10 carbon atoms substituted with an aryl group having 6 to 12 carbon atoms. Exemplary aralkyl groups often include an alkyl having 1 to 10 carbon atoms, 1 to 6 carbon atoms, or 1 to 4 carbon atoms substituted with a phenyl. Some $R^7$ groups combine with Q and the nitrogen atom to which $R^7$ is attached to form a heterocyclic group. The heterocyclic group often has at least 4, at least 5, or at least 6 ring atoms with the nitrogen atom being one of these ring atoms. The heterocyclic group can be unsaturated or partially saturated. One exemplary heterocyclic group is the divalent group derived from piperizine.

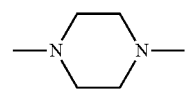

Some exemplary first amine compounds that can be included in the reaction mixture are polyether amines (i.e., the group Q is a heteroalkylene with oxygen heteroatoms). Such diamines are commercially available from Huntsman, The Woodlands, Tex. under the trade designation JEFFAMINE. Specific polyether amines include, but are not limited to, JEFFAMINE D-230 (i.e., polyoxypropylene diamine having a weight average molecular weight of about 230 grams/mole), JEFFAMINE D-400 (i.e., polyoxypropylene diamine having a weight average molecular weight of about 400 grams/mole), JEFFAMINE D-2000 (i.e., polyoxypropylene diamine having a weight average molecular weight of about 2,000 grams/mole), JEFFAMINE HK-511 (i.e., polyetherdiamine with both oxyethylene and oxypropylene groups and having a weight average molecular weight of about 220 grams/mole), JEFFAMINE ED-2003 (i.e., polyether diamine with a polypropylene oxide segment capped polyethylene glycol and having a weight average molecular weight of about 2,000 grams/mole), JEFFAMINE EDR-148 (i.e., triethyleneglycol diamine), and JEFFAMINE XTJ-559 (i.e., polyether diamine copolymer of polytetramethylene ether glycol (PTMEG) and polypropylene oxide having an average molecular weight of about 1,400 grams/mole).

Exemplary alkylene diamines (i.e., Q is an alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine (also called isophorene diamine).

Exemplary arylene diamines (i.e., Q is an arylene such as phenylene) include, but are not limited to, m-phenylene diamine, o-phenylene diamine, and p-phenylene diamine. Exemplary aralkylene diamines (i.e., Q is an aralkylene such as alkylene-phenyl) include, but are not limited to 4-aminomethyl-phenylamine, 3-aminomethyl-phenylamine, and 2-aminomethyl-phenylamine. Exemplary alkylene-aralkylene diamines (i.e., Q is a alkylene-arylene-alkylene group) include, but are not limited to, 4-aminomethyl-benzylamine (i.e, para-xylene diamine), 3-aminomethyl-benzylamine (i.e., meta-xylene diamine), and 2-aminomethyl-benzylamine (i.e., ortho-xylene diamine).

Other diamines have one or more secondary amino groups that are part of a heterocyclic group. Examples include, but are not limited to, piperizine.

Reaction Scheme B shows the exemplary reaction of a fluorinated oxalylamino-containing compound of Formula (VI) and the first amine compound of Formula (IIa). More than one first amine compound can be used. The group $Q^1$ is equal to the group —$Y^1$—Rf—$Y^1$— in Formula (VI).

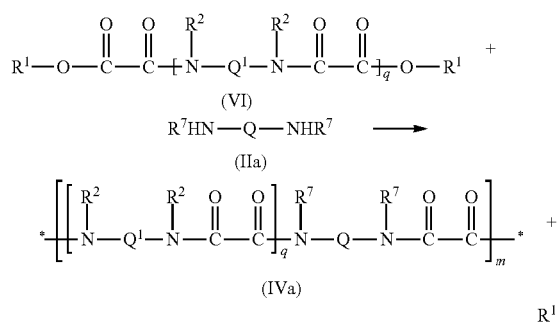

Reaction Scheme B

In the copolymer product of Formula (IVa), m is an integer equal to at least 1, at least 2, at least 3, at least 5, or at least 10. The variable m can be, for example, up to 1000, up to 500, up to 200, up to 100, up to 50, or up to 20. Each q can be equal to at least 1, at least 2, or at least 5. Variable q can be, for example, up to 100, up to 50, up to 20, or up to 10. In some embodiments, the variable q can be in the range of 1 to 20, in the range of 2 to 20, in the range of 1 to 10, or in the range of 2 to 10. Each asterisk denotes the attachment to any other group in the copolymer. This other group can be, for example, another group of Formula (IVa), an end group, or yet another segment in the copolymeric structure.

In addition to the first amine compound, other optional second amine compounds can be include in the first reaction mixture. For example, the first reaction mixture can include a fluorinated amine having a perfluoropolyether segment such as those of Formula (VII), (VIII), (VIIa), or (VIIIa). The fluorinated amine has at least two primary amino groups, at least two secondary amino groups, or at least one primary amino group plus at least one secondary amino group. If such a fluorinated amine is added, it can be of the same composition as the fluorinated amine used to form the fluorinated oxalylamino-containing compound or any other fluorinated amine. Although the optional second amine does not include a polydiorganosiloxane segment, most other suitable second amine compounds can be used. If a crosslinked polymeric material is desired, either the first amine compound or the optional second amine compound can be used to provide that crosslinking.

In the first reaction mixture, the ratio of the equivalents of the fluorinated oxalylamino-containing compound to the equivalents of the first amine compound plus any optional second amine compound is often about 1:1. For example the equivalents ratio is often less than or equal to 1:0.90, less than or equal to 1:0.92, less than or equal to 1:0.95, less than or equal to 1:0.98, or less than or equal to 1:1. The equivalents ratio is often greater than or equal to 1:1.02, greater than or equal to 1:1.05, greater than or equal to 1:1.08, or greater than or equal to 1:1.10. For example, the equivalents ratio can be in the range of 1:0.90 to 1:1.10, in the range of 1:0.92 to 1:1.08, in the range of 1:0.95 to 1:1.05, or in the range of 1:0.98 to 1:1.02. Varying the equivalents ratio can be used, for example, to alter the overall molecular weight, which can affect the rheology of the resulting copolymers. Additionally, varying the equivalents ratio can be used to provide oxalylamino-containing end groups or amino end groups, depending upon which reactant is present in excess.

The condensation reaction of Reaction Scheme B is often conducted at room temperature or at elevated temperatures such as at temperatures up to about 250° C. For example, the reaction often can be conducted at room temperature or at temperatures up to about 100° C. In other examples, the reaction can be conducted at a temperature of at least 100° C., at least 120° C., or at least 150° C. For example, the reaction temperature is often in the range of 100° C. to 220° C., in the range of 120° C. to 220° C., or in the range of 150° C. to 200° C. The condensation reaction is often complete in less than 1 hour, in less than 2 hours, in less than 4 hours, in less than 8 hours, or in less than 12 hours.

Reaction Scheme B can occur in the presence or absence of a solvent. Conducting Reaction Scheme B in the absence of a solvent can be desirable because only the volatile by-product $R^1OH$ needs to be removed at the conclusion of the reaction. Additionally, a solvent that is not compatible with both reactants and the product can result in incomplete reaction and a low degree of polymerization. In some applications, however, the copolymer will be used in a solvent-based coating composition. In such applications, it can be desirable to prepare the copolymer in the presence of a solvent.

Suitable solvents usually do not react with any of the reactants or products of the reactions. Additionally, suitable solvents are usually capable of maintaining all the reactants and all of the products in solution throughout the polymerization process. Exemplary solvents include, but are not limited to, toluene, tetrahydrofuran, dichloromethane, ethyl acetate, trifluoroethanol, trifluorotoluene, tert-butyl methyl ether, hexafluoroisopropanol, aliphatic hydrocarbons (e.g., alkanes such as hexane), or mixtures thereof.

Any solvent that is present can be stripped from the resulting copolymeric reaction product. Solvents that can be removed under the same conditions used to remove the by-product $R^1$—OH are often preferred. The stripping process is often conducted at a temperature of at least 100° C., at least 125° C., or at least 150° C. The stripping process is typically at a temperature less than 300° C., less than 250° C., or less than 225° C.

Any suitable reactor or process can be used to prepare the copolymer according to Reaction Scheme B. The reaction can be conducted using a batch process, semi-batch process, or a continuous process. Exemplary batch processes can be conducted in a reaction vessel equipped with a mechanical stirrer such as a Brabender mixer, which is commercially available from C.W. Brabender Instruments, Inc. (South Hackensack, N.J.), provided the product of the reaction in a molten state has a sufficiently low viscosity to be drained from the reactor. Exemplary semi-batch process can be conducted in a continuously stirred tube, tank, or fluidized bed. Exemplary continuous processes can be conducted in a single screw or twin screw extruder such as a wiped surface counter-rotating or co-rotating twin screw extruder.

In many processes, the components are metered and then mixed together to form a reaction mixture. The components can be metered volumetrically or gravimetrically using, for example, a gear, piston, or progressing cavity pump. The components can be mixed using any known static or dynamic method such as, for example, static mixers, or compounding mixers such as single or multiple screw extruders. The reaction mixture can then be formed, poured, pumped, coated, injection molded, sprayed, sputtered, atomized, stranded or sheeted, and partially or completely polymerized. The partially or completely polymerized material can then optionally be converted to a particle, droplet, pellet, sphere, strand, ribbon, rod, tube, film, sheet, coextruded film, web, nonwoven, microreplicated structure, or other continuous or discrete shape, prior to the transformation to solid polymer. Any of these steps can be conducted in the presence or absence of applied heat. In one exemplary process, the components can be metered using a gear pump, mixed using a static mixer, and injected into a mold prior to solidification of the polymerizing material.

In the second reaction mixture used to form the copolymer, the compound having at least two oxalylamino-containing groups of Formula (I) is a second oxalylamino-containing compound that does not contain a perfluoropolyether segment. This second oxalylamino-containing compound is reacted with a fluorinated amine having a perfluoropolyether segment and at least two primary amino groups, at least two secondary amino groups, or a combination of at least one primary amino group plus at least one secondary amino group.

The first reaction mixture and the second reaction mixture are complementary reaction mixtures. In the first reaction mixture, the oxalylamino-containing groups of Formula (I) are on a fluorinated compound having a perfluoropolyether segment. This fluorinated oxalylamino-containing compound is reacted with a first amine compound having multiple primary and/or secondary amino groups (i.e., at least two primary amino groups, at least two secondary amino groups, or at least one primary amino group plus at least at least one secondary amino group). The first amine compound does not have a perfluoropolyether segment. This reaction is exemplified in Reaction Scheme B above. In the second reaction mixture, the oxalylamino-containing groups of Formula (I) are on a second oxalylamino-containing compound that does not have a perfluoropolyether segment. This second oxalylamino-containing compound is reacted with a fluorinated amine having a perfluoropolyether segment as well as multiple primary and/or secondary amino groups. This reaction is exemplified in Reaction Scheme D below. A similar type of copolymer can be prepared using either the first reaction mixture or the second reaction mixture.

The second oxalylamino-containing compound is of Formula (XII).

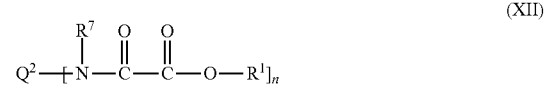

(XII)

The groups $Q^2$, $R^7$, and $R^1$ as well as the variable n are the same as previously described.

In many embodiments, the second oxalylamino-containing compound included in the second reaction mixture is often of Formula (III).

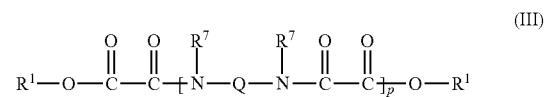

(III)

In Formula (III), each $R^1$ is independently an alkyl, haloalkyl, aralkyl, substituted aralkyl, alkenyl, aryl, substituted aryl, or imino of formula $-N=CR^4R^5$. Each $R^7$ is independently hydrogen, alkyl, aralkyl, aryl, or part of a heterocyclic group that includes Q and a nitrogen to which $R^7$ is attached. Group $R^4$ is hydrogen, alkyl, aralkyl, substituted aralkyl, aryl, or substituted aryl. Group $R^5$ is an alkyl, aralkyl, substituted aralkyl, aryl, or substituted aryl. Group Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^2$ is attached, or (g) a combination thereof. The groups $R^1$, $R^7$, and Q are the same as described above. The variable p is an integer equal to at least 1.

The compound of Formula (III) can be prepared by the reaction of an oxalate of Formula (IX) with a first amine compound of Formula (IIa). This condensation reaction is shown in Reaction Scheme C.

Reaction Scheme C

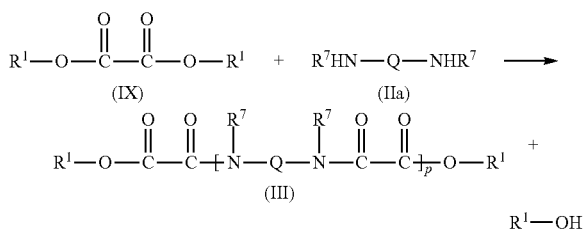

As with Reaction Scheme A, the condensation reaction exemplified in Reaction Scheme C can occur in the presence or in the absence of a solvent. In some synthesis methods, no solvent or only a small amount of solvent is included in the reaction mixture. The absence of a solvent can be desirable when the removal of the solvent would be advantageous for the subsequent use of the product of the condensation reaction. In other synthesis methods, a solvent may be included such as, for example, toluene, tetrahydrofuran, dichloromethane, or aliphatic hydrocarbons (e.g., alkanes such as hexane).

An excess (e.g., an excess based on equivalents) of the oxalate compound of Formula (IX) is typically used to form the second oxalylamino-containing compound of Formula (III). The excess can typically be removed from the desired reaction product of the condensation reaction using a stripping process similar to that described for Reaction Scheme A. The by-product of the condensation reaction is of formula $R^1$—OH, which is typically an alcohol, phenol, or oxime. Group $R^1$ is often selected to produce an alcoholic by-product that can be removed (e.g., vaporized) by heating at temperatures no greater than about 250° C. Such a by-product can be removed when the reacted mixture is heated to remove any excess oxalate compound of Formula (IX).

Once formed, the second oxalylamino-containing compound of Formula (III) can undergo a condensation reaction with a fluorinated amine. Suitable fluorinated amines have a perfluoropolyether segment and are the same as those described previously with at least two primary amino groups, at least two secondary amino groups, or at least one primary amino group plus at least one secondary amino group. Such fluorinated amines are those, for example, of Formula (VII), (VIIa), (VIII), or (VIIIa). Reaction Scheme D shows the exemplary reaction of a second oxalylamino-containing compound of Formula (III) with a fluorinated amine of Formula (VIIa) with $Q^1$ equal to the divalent group —$Y^1$—Rf—$Y^1$—. More than one fluorinated amine can be used. The product is a copolymer having at least one group of Formula (IVb).

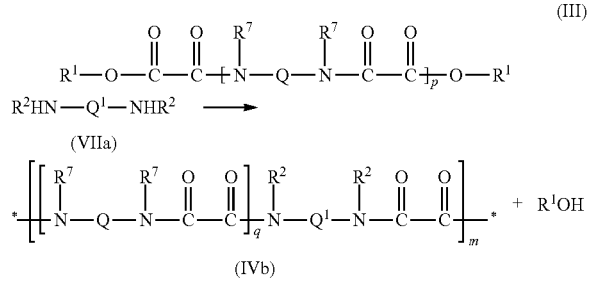

Reaction Scheme D

In the copolymeric product of Formula (IVb), m is an integer equal to at least 1, at least 2, at least 3, at least 5, or at least 10. The variable m can be, for example, up to 1000, up to 500, up to 200, up to 100, up to 50, or up to 20. Each p can be equal to at least 1, at least 2, or at least 5. Variable p can be, for example, up to 100, up to 50, up to 20, or up to 10. In some embodiments, the variable p can be in the range of 1 to 20, in the range of 2 to 20, in the range of 1 to 10, or in the range of 2 to 10. Each asterisk denotes the attachment to any other group in the copolymer. This other group can be, for example, another group of Formula (IVb), an end group, or yet another unit in the copolymeric structure.

In addition to the fluorinated amine having a perfluoropolyether segment, other optional second amine compounds can be include in the second reaction mixture. For example, the second reaction mixture can include an amine compound of Formula (II) or (IIa). The optional second amine compound can be the same compound used to form the second oxalylamino-containing compound or can be a different compound. Although the second amine compound does not contain a polydiorganosiloxane segment, most other suitable second amine compounds can be used. If crosslinking of the polymeric material is desired, the optional second amine can include more than two primary and/or secondary amino groups.

In the second reaction mixture, the ratio of the equivalents of the second oxalylamino-containing compound to the equivalents of the fluorinated amine plus any optional second amine compound is often about 1:1. For example the equivalents ratio is often less than or equal to 1:0.90, less than or equal to 1:0.92, less than or equal to 1:0.95, less than or equal to 1:0.98, or less than or equal to 1:1. The equivalents ratio is often greater than or equal to 1:1.02, greater than or equal to 1:1.05, greater than or equal to 1:1.08, or greater than or equal to 1:1.10. For example, the equivalents ratio can be in the range of 1:0.90 to 1:1.10, in the range of 1:0.92 to 1:1.08, in the range of 1:0.95 to 1:1.05, or in the range of 1:0.98 to 1:1.02. Varying the equivalents ratio can be used, for example, to alter the overall molecular weight, which can affect the rheology of the resulting copolymers. Additionally, varying the equivalents ratio can be used to provide oxalylamino-containing end groups or amino end groups, depending upon which reactant is present in excess.

The same process conditions described for Reaction Scheme B can be used for Reaction Scheme D. More specifically, the condensation reaction is often conducted at room temperature or at elevated temperatures such as at temperatures up to about 250° C. The condensation reaction is often complete in 1 hour, in 2 hours, in 4 hours, in 8 hours, in 12 hours, in 24 hours, in 36 hours, in 48 hours, in 56 hours, in 72 hours, or longer. Any suitable reactor or process can be used.

The condensation reaction of Reaction Scheme D can occur in the presence or absence of a solvent. Suitable solvents usually do not react with any of the reactants or products of the reactions. Additionally, suitable solvents are usually capable of maintaining all the reactants and all of the products in solution throughout the polymerization process. Exemplary solvents include, but are not limited to, toluene, tetrahydrofuran, dichloromethane, aliphatic hydrocarbons (e.g., alkanes such as hexane), or mixtures thereof. Any solvent that is present can be stripped from the resulting copolymer at the completion of the reaction. Solvents that can be removed under the same conditions used to remove the alcohol by-product are often preferred.

Silicone-based amines are typically not included in either the first reaction mixture or the second reaction mixture. Likewise, the resulting copolymer typically does not contain polydiorganosiloxane segments.

In a third aspect, a copolymer is provided. The copolymer includes a product of a third reaction mixture that includes an oxalate compound, a fluorinated amine compound, and a first amine compound. The oxalate compound is of Formula (IX).

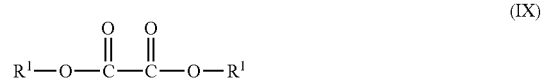

In Formula (IX), each $R^1$ is independently an alkyl, haloalkyl, aralkyl, substituted aralkyl, alkenyl, aryl, substituted aryl, or imino of formula —N=$CR^4R^5$. Group $R^4$ is hydrogen, alkyl, aralkyl, substituted aralkyl, aryl, or substituted aryl. Group $R^5$ is alkyl, aralkyl, substituted aralkyl, aryl, or substituted aryl. The fluorinated amine contains a perfluoropolyether segment and at least two primary amino groups, at least two secondary amino groups, or at least one primary amino group plus at least one secondary amino group. The first amine compound is of Formula (II).

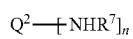
(II)

In Formula (II), group $Q^2$ is (a) an alkane radical, (b) a fluorinated alkane radical, (c) a heteroalkane radial, (d) an arene radical, (e) a carbonylamino group linking a first group to a second group, where each first group and second group is independently an alkane radical, a fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each group $R^7$ is independently hydrogen, alkyl, aralkyl, aryl, or part of a heterocyclic group that includes $Q^2$ and the nitrogen to which $R^7$ is attached. The variable n is an integer equal to at least 2.

In many embodiments of the first amine compound of Formula (II), the variable n is equal to two and the compound is of Formula (IIa).

$$R^7HN-Q-NHR^7 \quad (IIa)$$

In Formula (IIa), the group Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and a nitrogen to which $R^7$ is attached, or (g) a combination thereof. Each $R^7$ is independently hydrogen, alkyl, aralkyl, aryl, or part of a heterocyclic group that includes Q and the nitrogen atom to which $R^7$ is attached.

The method of forming a copolymer from the third reaction mixture is exemplified in Reaction Scheme E. The oxalate compound of Formula (IX) is reacted in the presence of multiple amines. The amines include a fluorinated amine having a perfluoropolyether segment of Formula (VIIa) and a first amine compound of Formula (IIa). The copolymer is of Formula (IV). The copolymers prepared from the third reaction mixture tend to be more random than copolymers prepared from the first reaction mixture or the second reaction mixture.

Reaction Scheme E

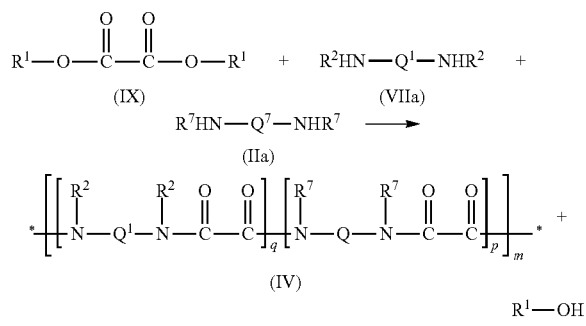

The reaction mixture can include more than one fluorinated amine and more than one first amine compound. The same conditions used to form the fluorinated oxalylamino-containing compound in Reaction Scheme A or to form the silicone-based oxalylamino-containing compound in Reaction Scheme C can be used. Any method described for removing any excess oxalate compound or the byproducts of formula $R^1$—OH can be used with this method of preparing the copolymer.

In embodiments where a crosslinked polymeric material is desired, at least one of the fluorinated amine compound or the first amine compound is usually selected to have more than two primary and/or secondary amino groups.

In the third reaction mixture, the ratio of equivalents of the oxalate compound to the total equivalents of the amine compounds (fluorinated amine plus first amine compound) is often about 1:1. For example the equivalents ratio is often less than or equal to 1:0.90, less than or equal to 1:0.92, less than or equal to 1:0.95, less than or equal to 1:0.98, or less than or equal to 1:1. The equivalents ratio is often greater than or equal to 1:1.02, greater than or equal to 1:1.05, greater than or equal to 1:1.08, or greater than or equal to 1:1.10. For example, the equivalents ratio can be in the range of 1:0.90 to 1:1.10, in the range of 1:0.92 to 1:1.08, in the range of 1:0.95 to 1:1.05, or in the range of 1:0.98 to 1:1.02. Varying the equivalents ratio can be used, for example, to alter the overall molecular weight, which can affect the rheology of the resulting copolymers. Additionally, varying the equivalents ratio can be used to provide oxalylamino-containing end groups or amino end groups, depending upon which reactant is present in excess (e.g., an excess based on equivalents).

In a fourth aspect, a copolymer is provided. The copolymer contains at least one group of Formula (IV).

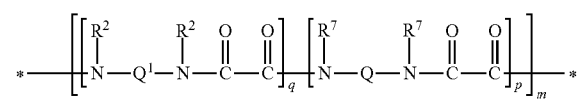
(IV)

In Formula (IV), each group $Q^1$ contains a perfluoropolyether segment. Each group Q is the same as previously described. The group $R^2$ is the same as described previously for Formula (V). The group $R^7$ is the same as described previously for Formula (IIa). Each variable q, p, and m is an integer equal to at least 1. For example, the variable m can be equal to at least 2, at least 3, at least 5, or at least 10. The variable m can be, for example, up to 1000, up to 500, up to 200, up to 100, up to 50, or up to 20. Each variable q and p can be equal to at least 1, at least 2, or at least 5. These variable q and p can be, for example, up to 100, up to 50, up to 20, or up to 10. In some embodiments, the variables q and p can be in the range of 1 to 20, in the range of 2 to 20, in the range of 1 to 10, or in the range of 2 to 10. Group $R^2$ is the same as described for Formula (I). Each asterisk denotes a site of attachment to another group in the copolymer.

The copolymer of Formula (IV) is equal to the copolymer of Formula (IVa) when p is equal to 1 and is equal to the copolymer of Formula (IVb) when q is equal to 1. These copolymers do not contain a polydiorganosiloxane segment.

Group $Q^1$ is a perfluoropolyether group and is typically a divalent group of Formula (X).

$$—Y^1—Rf—Y^1— \quad (X)$$

Groups Rf and $Y^1$ are the same are previously described. In some embodiments of Formula (X), group $Q^1$ is of formula (XI).

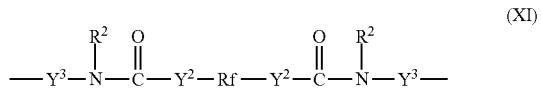 (XI)

Groups Rf, $Y^1$, $Y^2$, $Y^3$, and $R^2$ being the same as previously described. In some more particular embodiments of either (X) or (XI), the group Rf can be of formula

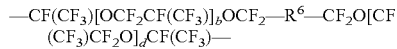

where $R^6$, b, and d are the same as previously described.

The copolymers of Formulas (IV), (IVa), and (IVb) can be cast from solvents as film, molded or embossed in various shapes, or extruded into films. The high temperature stability of the copolymers makes them well suited for extrusion methods of film formation.

Various articles can be prepared that contain the polymer of Formulas (IV), (IVa), or (IVb). The article, for example, can include a layer containing the copolymer of Formulas (IV), (IVa), or (IVb) and one or more optional substrates. For example, the copolymer of Formulas (IV), (IVa), or (IVb) can be in a layer adjacent to a first substrate or positioned between a first substrate and a second substrate. That is, the article can be arranged in the following order: a first substrate, a layer containing the copolymer of Formulas (IV), (IVa), or (IVb) and a second substrate. As used herein, the term "adjacent" refers to a first layer that contacts a second layer or that is positioned in proximity to the second layer but separated from the second layer by one or more additional layers.

The copolymers include the aminooxalylamino groups that are capable of hydrogen bonding. The copolymers have increased hydrogen bonding compared to many perfluoropolyether materials. This increased hydrogen bonding can give additional strength and rigidity to the copolymer. Many perfluoropolyether materials are relatively soft.

These copolymers can be used, for example, in applications where abrasion resistance is desired. Additionally, these copolymers often can be subjected to temperatures as high as 250° C. with minimal degradation. The copolymers can be used in applications where materials having low refractive index, low surface energy, oil and/or water repellency, or a combination thereof are desired. The copolymers can be used to form antireflective coatings or films. Films or coatings containing the copolymers are usually easily cleaned.

Various items are provided that are copolymers.

A first item is provided that is a copolymer that includes the product of a reaction mixture. The reaction mixture includes a) a fluorinated oxalylamino-containing compound and b) a first amine compound. The fluorinated oxalylamino-containing compound contains at least one perfluoropolyether segment and at least two monovalent oxalylamino-containing groups of Formula (Ia).

 (Ia)

In Formula (Ia), each $R^1$ is independently an alkyl, haloalkyl, aralkyl, substituted aralkyl, alkenyl, aryl, substituted aryl, or imino of formula $-N=CR^4R^5$. Each $R^4$ is hydrogen, alkyl, aralkyl, substituted aralkyl, aryl, or substituted aryl. Each $R^5$ is alkyl, aralkyl, substituted aralkyl, aryl, or substituted aryl. Each $R^2$ is independently hydrogen, alkyl, aralkyl, or aryl. The first amine compound is of Formula (II).

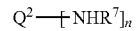 (II)

In Formula (I), $Q^2$ is (a) an alkane radical, (b) a fluorinated alkane radical, (c) a heteroalkane radical, (d) an arene radical, (e) a carbonylamino group linking a first group to a second group, where each first group and second group is independently an alkane radical, a fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each group $R^7$ is independently hydrogen, alkyl, aralkyl, aryl, or part of a heterocyclic group that includes $Q^2$ and the nitrogen to which $R^7$ is attached. The variable n is an integer equal to at least 2.

A second item is provided that can be a version of the first item. In the second item, the fluorinated oxalylamino-containing compound is of Formula (V).

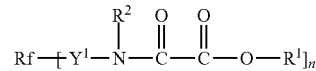 (V)

In Formula (V), Rf is a perfluoropolyether group. Each $Y^1$ is independently (a) a heteroalkylene, (b) alkylene, (c) a carbonylamino group linking a first group to a second group, wherein the first group and the second group are each independently a heteroalkylene or alkylene, or (d) a combination thereof. The variable n is an integer greater than or equal to at least 2.

A third item is provided that can be a version of the second item. In the third item, the fluorinated oxalylamino-containing compound is of Formula (Va).

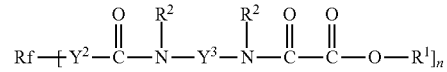 (Va)

In Formula (Va), each $Y^1$ in Formula (V) is equal to $-Y^2-(CO)-NH-Y^3-$ in Formula (Va). Each $Y^2$ is independently a single bond, heteroalkylene, alkylene, or combination thereof. Each $Y^3$ is independently a heteroalkylene, alkylene, or combination thereof.

A fourth item is provided that can be a version of the first item. In the fourth item, the fluorinated oxalylamino-containing compound is of Formula (VI).

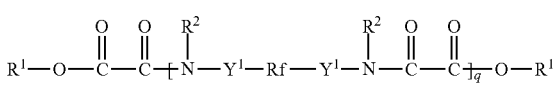 (VI)

In Formula (VI), Rf is a perfluoropolyether group. Each $Y^1$ is independently (a) a heteroalkylene, (b) alkylene, (c) a carbonylamino group linking a first group to a second group, wherein the first group and the second group are each independently a heteroalkylene or alkylene, or (d) a combination thereof. The variable q is an integer equal to at least 1.

A fifth item is provided that can be a version of the fourth item. In the fifth item, the fluorinated oxalylamino-containing compound is of Formula (VIa).

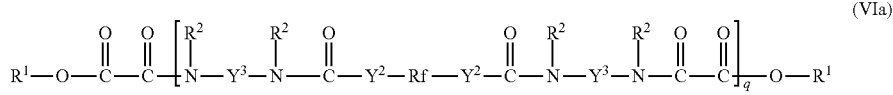

Each $Y^1$ in Formula (VI) is equal to —$Y^2$—(CO)—NH—$Y^3$— in Formula (VIa). Each $Y^2$ is independently a single bond, heteroalkylene, alkylene, or combination thereof. Each $Y^3$ is independently a heteroalkylene, alkylene, or combination thereof.

A sixth item is provided that can be a version of any one of the second to fifth items. In the sixth item, Rf is of the following formula.

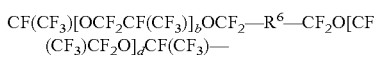

In this formula, $R^6$ is a perfluoroalkylene group. The variable b and d are integers with a sum in the range of 0 to 35.

A seventh item is provided that can be a version of any one of the first to sixth items. In the seventh item, the first amine compound is of Formula (IIa).

In Formula (IIa), Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^7$ is attached, or (g) a combination thereof. Each $R^7$ is independently hydrogen, alkyl, aralkyl, aryl, or part of a heterocyclic group that includes Q and the nitrogen atom to which $R^7$ is attached.

An eighth item is provided that includes a product of a reaction mixture. The reaction mixture includes a) a second oxalylamino-containing compound and b) a fluorinated amine having a perfluoropolyether segment and having at least two primary amino groups, two secondary amino groups, or a mixture thereof. The second oxalylamino-containing compound is of Formula (III).

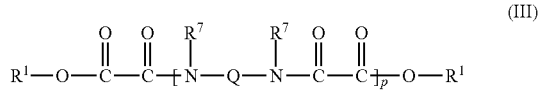

In Formula (III), each $R^1$ is independently an alkyl, haloalkyl, aralkyl, substituted aralkyl, alkenyl, aryl, substituted aryl, or imino of formula —N=$CR^4R^5$. Group $R^4$ is hydrogen, alkyl, aralkyl, substituted aralkyl, aryl, or substituted aryl. Group $R^5$ is an alkyl, aralkyl, substituted aralkyl, aryl, or substituted aryl. Each $R^7$ is independently hydrogen, alkyl, aralkyl, aryl, or part of a heterocyclic group that includes Q and a nitrogen to which $R^7$ is attached. Group Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^7$ is attached, or (g) a combination thereof. The variable p is an integer equal to at least 1.

A ninth item is provided that can be a version of the eighth item. In the ninth item, the fluorinated amine is of Formula (VII).

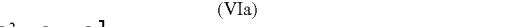

In Formula (VII), Rf is a perfluoropolyether group. Each $Y^1$ is independently (a) a heteroalkylene, (b) alkylene, (c) a carbonylamino group linking a first group to a second group, wherein the first group and the second group are each a heteroalkylene or alkylene, or (d) a combination thereof. The variable n is an integer equal to at least 1.

A tenth item is provided that can be a version of the ninth item. In the tenth item, the fluorinated amine is of Formula (VII).

Each $Y^1$ in Formula (VII) is equal to —$Y^2$—(CO)—NH—$Y^3$— in Formula (VIII). Each $Y^2$ is independently a single bond, heteroalkylene, alkylene, or combination thereof. Each $Y^3$ is independently a heteroalkylene, alkylene, or combination thereof.

An eleventh item is provided that can be a version of the ninth or tenth items. In the eleventh item, Rf is of the following formula.

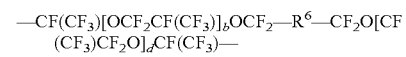

In this formula, $R^6$ is a perfluoroalkylene group. The variables b and d are integers with a sum in the range of 0 to 35.

A twelfth item is provided that is a copolymer. The copolymer contains at least one group of Formula (IV).

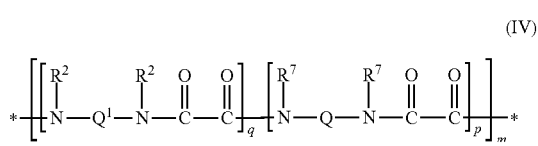

In Formula (IV), each group $Q^1$ contains a perfluoropolyether segment. Each Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^7$ is attached, or (g) a combination thereof.

Each group $R^2$ is independently hydrogen, alkyl, aralkyl, or aryl. Each $R^7$ is independently hydrogen, alkyl, aralkyl, aryl, or a part of a heterocyclic group that includes Q and the nitrogen to which $R^7$ is attached. Each variable q, p, and m is independently an integer equal to at least 1. Each asterisk denotes a site of attachment to another group in the copolymer.

A thirteenth item is provided that can be a version of the twelfth item. In the thirteenth item, $Q^1$ is a divalent group of Formula (X).

  (X)

In Formula (X), each $Y^1$ is independently (a) a heteroalkylene, (b) alkylene, or (c) a carbonylamino group linking a first group to a second group, wherein the first group and the second group are each a heteroalkylene or alkylene, or (d) a combination thereof. The group Rf is a perfluoropolyether group.

A fourteenth item is provided that can be a version of the thirteenth item. In the fourteenth item, $Q^1$ is the divalent group of Formula (XI).

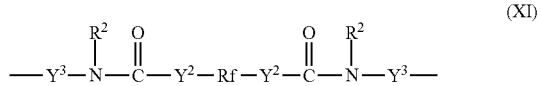  (XI)

In Formula (XI), each $Y^2$ is independently a single bond, heteroalkylene, alkylene, or combination thereof. Each $Y^3$ is independently a heteroalkylene, alkylene, or combination thereof.

A fifteenth item is provided that can be a version of the thirteenth or fourteenth item. In the fifteenth item, Rf is of the following formula.

—CF(CF$_3$)[OCF$_2$CF(CF$_3$)]$_b$OCF$_2$—R$^6$—CF$_2$O[CF(CF$_3$)CF$_2$O]$_d$CF(CF$_3$)—

In this formula, $R^6$ is a perfluoroalkylene group. The variable b and d are integers with a sum in the range of 0 to 35.

A sixteenth item is provided that can be a version of any one of the twelfth to fifteenth items. In the sixteenth item, at least one of p or q is equal to 1.

A seventeenth item is provided that include a product of a reaction mixture. The reaction mixture includes a) an oxalate compound, b) a fluorinated amine having a perfluoropolyether segment and having at least two primary amino groups, two secondary amino groups, or a mixture thereof, and c) a first amine compound. The oxalate compound is of Formula (IX).

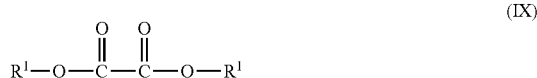  (IX)

In Formula (IX), each $R^1$ is independently an alkyl, haloalkyl, aralkyl, substituted aralkyl, alkenyl, aryl, substituted aryl, or imino of formula —N=CR$^4$R$^5$. Group $R^4$ is hydrogen, alkyl, aralkyl, substituted aralkyl, aryl, or substituted aryl. Group $R^5$ is alkyl, aralkyl, substituted aralkyl, aryl, or substituted aryl. The first amine compound of Formula (II).

  (II)

In Formula (II), $Q^2$ is (a) an alkane radical, (b) a fluorinated alkane radical, (c) a heteroalkane, (d) derived from an arene radical, (e) a carbonylamino group linking a first group to a second group, where each first group and second group is independently an alkane radical, a fluorinated alkane radical, a heteroalkylene radical, an arene radical, or a combination thereof, (f) part of a heterocyclic group that includes $R^7$ and a nitrogen to which $R^7$ is attached, or (g) a combination thereof. Each $R^7$ is independently hydrogen, alkyl, aralkyl, aryl, or part of a heterocyclic group that includes $Q^2$ and the nitrogen to which $R^7$ is attached. The variable n is an integer equal to at least 2.

An eighteenth item is provided that can be a version of the seventeenth item. In the eighteenth item, the first amine compound is of Formula (IIa).

  (IIa)

In Formula (IIa), group Q is (a) a heteroalkylene, (b) alkylene, (c) fluorinated alkylene, (d) arylene, (e) a carbonylamino group linking a first group to a second group, where each first group and second group is independently a heteroalkylene, alkylene, fluorinated alkylene, arylene, or a combination thereof, (f) part of a heterocyclic group that includes $R^7$ and the nitrogen to which $R^2$ is attached, or (g) a combination thereof. Each $R^7$ is independently hydrogen, alkyl, aralkyl, aryl, or part of a heterocyclic group that includes Q and the nitrogen atom to which $R^7$ is attached.

EXAMPLES

These examples are for illustrative purposes only and are not meant to be limiting on the scope of the appended claims. All parts, percentages, and ratios in the examples are by weight unless otherwise noted. Solvents and other reagents used can be obtained from Sigma-Aldrich Chemical Company (Milwaukee, Wis.) unless otherwise noted.

As used herein, the term "HFPO" refers to monovalent or divalent poly(hexafluoropropylene oxide) segment. In some embodiments the HFPO segment is a monovalent group of formula

where a in an integer in the range of about 4 to about 20 or is a divalent group of formula

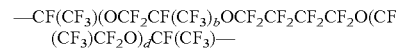

where the sum (b+d) is an integer in the range of about 4 to about 15.

Preparatory Example 1

Synthesis of H$_3$CO(CO)—HFPO—(CO)OCH$_3$

A dimethyl ester of poly(hexafluoropropylene oxide) was prepared using F(CO)CF$_2$CF$_2$(CO)F as an starting material according to the method reported in U.S. Pat. No. 3,250,807 (Fritz, et al.) which provides the HFPO oligomer bis-acid fluoride. The HFPO oligomer bis-acid fluoride was subjected to methanolysis and purification by removal of lower boiling materials by fractional distillation as described in U.S. Pat.

No. 6,923,921 (Flynn, et. al.). The resulting material was of formula

H₃CO(CO)CF(CF₃)(OCF₂CF(CF₃))ᵦ
OCF₂CF₂CF₂O(CF(CF₃)CF₂O)_dCF(CF₃)
(CO)OCH₃ where the sum (b+d) is an integer in the range of about 4 to about 15. This formula is also be referred to interchangeably as H₃CO(CO)—HFPO—(CO)OCH₃ or HFPO—((CO)OCH₃)₂ or HFPO dimethyl ester or HFPO-DME.

More specifically, to a 600-mL jacketed reactor, which is commercially available under the trade designation PARR from Parr Instrument Company (Moline, Ill.), was charged with KF (15.1 grams, 0.26 moles) and tetraglyme (125 grams). The reactor was stirred, evacuated to 0.033 atmosphere vacuum using a vacuum pump and cooled to 4° C. A charge of perfluorosuccinyl fluoride (85 grams, 0.44 moles) that was obtained from Exfluor Research Corporation (Austin, Tex.) was added to the reactor. External cooling was used to cool the contents of the reactor to 0° C. before adding hexafluoropropylene oxide (482 grams, 2.9 moles) slowly over 5 hours. The hexafluoropropylene oxide was obtained from DuPont (Wilmington, Del.). The maximum pressure was 2.38 atmospheres and an exotherm of 8° C. resulted. After addition was completed, the reactor was warmed to room temperature and nitrogen was used to break the 0.033 atmosphere reactor vacuum and to increase the pressure within the reactor to atmospheric pressure.

The crude mixture of 690 grams was drained from the reactor and reacted with methanol (120 grams, 3.8 moles) to convert the diacid fluoride ends to dimethyl ester end groups. The fluorochemical crude product was isolated by adding a fluorinated solvent (300 grams), which is commercially available under the trade designation FC77 FLUORINERT form 3M Company (Saint Paul, Minn.), and by water washing twice. The lower fluorochemical phase was stripped of fluorinated solvent and the product was isolated by taking a cut that boiled from 130-190° C. The yield was 390 grams (71 percent) of HFPO dimethyl ester having a weight average molecular weight of 1250 grams/mole and 96 percent functionality determined by NMR end group analysis.

Preparatory Example 2

Synthesis of H₂NCH₂CH₂—NH(CO)—HFPO—(CO)NH—CH₂CH₂NH₂

A 1 L 3-necked round bottom flask that was equipped with a magnetic stir bar, N₂ inlet and reflux condenser was charged with 420.0 grams NH₂—CH₂CH₂—NH₂ (7 moles) under N₂ atmosphere. The charge was heated to 75° C. Then the HFPO—[COOMe]₂ (150.0 grams, 8.75×10⁻² moles) of Preparatory Example 1 was added dropwise at 75° C. over a period of 180 minutes. The reaction mixture was stirred under N₂ atmosphere for 12 hours and the progress of the reaction was monitored by IR spectroscopy. After the disappearance of the ester peak at 1792 cm⁻¹ and appearance of the NH—C═O peak at 1719 cm⁻¹, the reaction mixture was poured onto a separation funnel and the lower portion was collected in a flask and dried under high vacuum for another 8 hours. The viscous oil obtained was used as such.

Preparatory Example 3

Synthesis of H₂N[CH₂CH₂O]₂CH₂CH₂NH(CO)—HFPO—(CO)NHCH₂CH₂[OCH₂CH₂]₂NH₂

A 1-L 3-necked round bottom flask was equipped with a magnetic stir bar, N₂ inlet and reflux condenser. The flask was charged with NH₂CH₂CH₂—O—CH₂CH₂—O—CH₂CH₂NH₂ (triethyleneglycol diamine—TEGDA) (52.9 grams 0.3 moles) under N₂ atmosphere. The charge was heated to 75° C. The HFPO-DME of Preparatory Example 1 (5.0 grams, 3.75×10⁻² moles) was added dropwise at 75° C. over a period of 180 minutes. The reaction mixture was stirred under N₂ atmosphere for 12 hours and was monitored by IR. After the disappearance of ester peak, the reaction mixture was poured onto a separation funnel and the lower portion was collected in a flask and dried under high vacuum for another 8 hours. The viscous oil obtained was used as such.

Preparatory Example 4

Synthesis of di(methyl ethyl ketoxime) oxalate

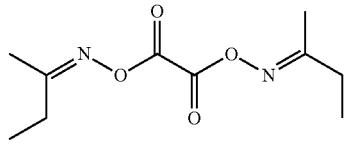 [SMILES: CC/C(C)=N\OC(=O)C(=O)O/N=C(\C)CC]

To a 1-L flask equipped with an overhead stirrer, addition funnel, ice bath, temperature probe, and nitrogen inlet was added 2-butanone oxime (93.23 grams, 1.070 moles) and butyl methyl ether (500 mL). The contents were cooled to 10° C., and oxalyl chloride (67.9 grams, 0.535 moles) was added over 30 minutes while maintaining the internal temperature below 15° C. Triethylamine (108 grams, 1.07 moles) was then added dropwise over 30 minutes with external cooling to maintain the internal temperature below 30° C. Enough water was added to dissolve the resulting solids, and then the aqueous layer was drawn off. The organic layer was washed twice with 0.1N HCl and once with 2M sodium carbonate, after which it was dried over MgSO₄ and filtered through a pad of Celite. The solvent was removed on a rotary evaporator to afford 120 grams of di(methyl ethyl ketoxime) oxalate as a clear, colorless oil. ¹H NMR (CDCl₃) was consistent with the proposed structure. The material was present as a mixture of stereoisomers.

Preparatory Example 5

Synthesis of N-{2-[(2,2,2-Trifluoroethoxyoxalyl)-amino]ethyl}-oxalamic acid 2,2,2-trifluoroethyl ester

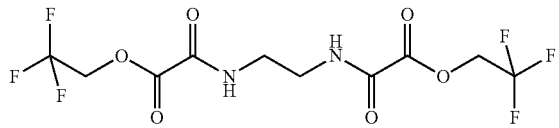 [SMILES: O=C(NCCNC(=O)C(=O)OCC(F)(F)F)C(=O)OCC(F)(F)F]

A 3-L 3-neck round bottom flask equipped with mechanical stirrer, addition funnel, temperature probe, and nitrogen inlet was charged with 2,2,2-trifluoroethanol (500 grams), t-butyl methyl ether (1300 mL), and pyridine (593 grams). The contents of the flask were cooled on an ice bath, and oxalyl chloride (317 grams) was added dropwise over a period of 1 hour while maintaining the internal temperature of the flask at less than 2° C. The reaction mixture was allowed to warm to ambient temperature and then stirred for 2 hours. Then the solids were removed by filtration. The filtrate was washed twice with 1 liter of cold 1 N hydrochloric acid, once with 1 liter of cold water, and once with 300 mL of 15 weight percent sodium carbonate solution. The organic layer was dried over anhydrous sodium sulfate and then concentrated on a rotary evaporator. The resulting oil was distilled at atmospheric pressure, and the fraction boiling at 159-163° C. was collected to obtain 245 grams of 2,2,2-trifluoroethyl oxalate as a clear, colorless oil.

A 500-mL 3-neck round bottom flask equipped with a magnetic stirring bar, thermocouple, and argon inlet was charged with 2,2,2-trifluoroethyl oxalate (152.5 grams) and 2,2,2-trifluoroethanol (150 grams). The contents of the flask were cooled in an ice bath, and a mixture of ethylene diamine (3.606 grams) in 2,2,2-trifluoroethanol (40 grams) was added dropwise over a period of 75 minutes. The cooling bath was removed, and the contents of flask were stirred for 18 hours. Then, tert-butyl methyl ether (100 mL) was added and the solids were collected via filtration. The resulting 10.2 grams of solid were recrystallized from boiling 2,2,2-trifluoroethanol (416 grams) to obtain 9.23 grams of N-{2-[(2,2,2-trifluoroethoxyoxalyl)-amino]-ethyl}-oxalamic acid 2,2,2-trifluoroethyl ester as white crystals with a melting point of 222-223° C. $^1$H NMR (300 MHz, d$_6$-DMSO) δ 9.18 (brs, 2H), 4.92 (q, J=8.9 Hz, 4H), 3.31-3.29 (m, 4H).

Preparatory Example 6

Synthesis of Fluorinated oxalylamino-Containing Compound

Into a 250-mL 3-necked flask was weighed dry diethyl oxalate (DEO) (64.9 grams). The flask was fitted with a stirrer and a gentle argon sweep of the flask was started. With vigorous stirring of the DEO, the fluorinated amine of Preparatory Example 3 (150.0 grams) was added dropwise from an addition funnel over about a period of 120 minutes. After all of the fluorinated amine was added, the additional funnel was removed and the flask was set up for distillation. Under high vacuum, the temperature was slowly increased from ambient to 165° C. The excess DEO and ethanol formed during the reaction were distilled out of the flask. About 147.38 grams (94.2 percent of the theoretical yield) of the oxalylamino ester terminated precursor product was isolated. Back titration of the product with ethanolamine and 1 N hydrochloric acid showed an ester equivalent weight of 1,950 grams/equivalent.

Preparatory Example 7

Synthesis of Fluorinated oxalylamino-Containing Compound

Into a 250-mL 3-necked flask was weighed dry diethyl oxalate (DEO) (87.7 grams, 1.20 equivalents). The flask was fitted with a stirrer and a gentle argon sweep of the flask was started. With vigorous stirring of the DEO the fluorinated diamine of Preparatory Example 4 (60.0 grams ($3.27 \times 10^{-2}$ equivalents), was added dropwise from an addition funnel over about a period of 75 minutes. After all of the fluorinated diamine was added, the addition funnel was removed and the flask was set up for distillation. Under high vacuum of 0.0013 atmospheres, the temperature was slowly increased from ambient to 165° C. The excess DEO and ethanol formed during the reaction were distilled out of the flask. About 65 grams (approximately 94.5 percent of the theoretical yield) of the oxalylamino ester terminated product was isolated. Back titration with ethanolamine and 1N HCl showed that the ester had an equivalent weight of 1,006 grams/equivalent.

Example 1

In a glass vial, the fluorinated oxalylamino-containing compound of Preparatory Example 7 (8.2375 grams, $8.19 \times 10^{-3}$ equivalent) was dissolved in hexafluoroisopropyl alcohol (HFIPA) (21.6 grams). Then a solution (1.8919 grams, $8.19 \times 10^{-3}$ equivalents) of ethylene diamine in tert-butylmethylether with a titrated amine equivalent weight of 231.05 grams of solution per equivalent, was added via a Gastight syringe. The reaction mixture was mixed overnight in a Launder-O-Meter (available from Atlas Electric Devices Co., Chicago, Ill.) at 55° C. and then on a roller for about 64 hours under ambient laboratory conditions. The polymer was dried in an aluminum weighing dish in a fume hood and then overnight at 60° C. The polymer obtained was a clear, brittle plastic.

Example 2

A glass vial was charged with the di(methyl ethyl ketoxime) oxalate (711.6 mg) of Preparatory Example 4 and 2,2,2-trifluoroethanol (20 grams). After mixing, material of Preparatory Example 3 with an amine equivalent weight of 1689.7 grams/equivalent, (5.0740 grams) was added. The vial was placed on a roller at ambient temperature for 1 hour. Ethylene diamine (91.0 mg) was added, and the vial was allowed to roll at ambient temperature for 15 hours. The solvent was removed in an oven at 125° C. for 45 minutes to prepare the product as a clear, tough polymer.

Example 3

N-{2-[(2,2,2-trifluoroethoxyoxalyl)-amino]-ethyl}-oxalamic acid 2,2,2-trifluoroethyl ester (500.6 mg) of Preparatory Example 5, the fluorinated amine of Preparatory Example 3 (4.535 grams, amine equivalent weight of 1689.7 grams/equivalent), and 2,2,2-trifluoroethanol (20 grams) were combined in a 20-mL glass vial and placed on a roller at ambient temperature for 2 days. The solvent was removed, by first using a stream of argon at ambient temperature and then placing the vial in an oven at 85° C. for 24 hours. The product was a clear, tough polymer.

Example 4

In a 120-mL glass jar, the fluorinated oxalylamino-containing material of Preparatory Example 6 (10.57 grams, $5.421 \times 10^{-3}$ equivalents) was combined with trifluoroethanol (42.93 grams) and mixed until homogeneous. Then ethylene diamine (0.1629 grams, $5.421 \times 10^{-3}$ equivalents) was added to the jar. The resulting reaction mixture was mixed for about one week under ambient conditions. The trifluoroethanol and ethanol by-product were removed using a stream of nitrogen and then placing the vial in an oven for 4 days at 60° C. The polymer obtained was a clear, colorless, tough elastomer.

We claim:

1. A copolymer comprising a product of a reaction mixture comprising:
   a) a second oxalylamino-containing compound of Formula (III)

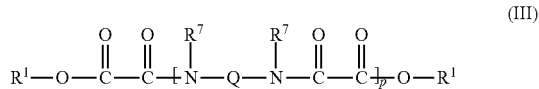

wherein
   each $R^1$ is independently an alkyl, haloalkyl, aralkyl, substituted aralkyl, alkenyl, aryl, substituted aryl, or imino of formula $—N=CR^4R^5$;
   each $R^7$ is independently hydrogen, alkyl, aralkyl, aryl, or part of a heterocyclic group that includes Q and a nitrogen to which $R^7$ is attached;
   $R^4$ is hydrogen, alkyl, aralkyl, substituted aralkyl, aryl, or substituted aryl;
   $R^5$ is an alkyl, aralkyl, substituted aralkyl, aryl, or substituted aryl;
   Q is (a) a heteroalkylene, (b) alkylene, (c) arylene, (d) a carbonylamino group linking a first group to a second group, where each first group and second group is independently a heteroalkylene, alkylene, arylene, or a combination thereof, (e) part of a heterocyclic group that includes $R^7$ and the nitrogen to which $R^7$ is attached, or (f) a combination thereof; and
   p is an integer equal to at least 1; and
   b) a fluorinated amine having a perfluoropolyether segment and having at least two primary amino groups, two secondary amino groups, or a mixture thereof
   wherein the fluorinated amine is of Formula (VII) or (VIII)

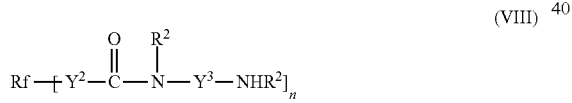

wherein
   Rf is a perfluoropolyether group; and
   each $Y^1$ is independently (a) a heteroalkylene having at least two carbon atoms, (b) alkylene having at least two carbon atoms, (c) a carbonylamino group linking a first group to a second group, wherein the first group and the second group are each a heteroalkylene having at least two carbon atoms or alkylene having at least two carbon atoms, or (d) a combination thereof;
   each $R^2$ is independently hydrogen, alkyl, aralkyl, or aryl;
   n is an integer equal to at least 1;
   each $Y^2$ is independently a single bond, heteroalkylene having at least two carbon atoms, alkylene having at least two carbon atoms, or combination thereof; and
   each $Y^3$ is independently a heteroalkylene having at least two carbon atoms, alkylene having at least two carbon atoms, or combination thereof.

2. The copolymer of claim 1, wherein Rf is of formula

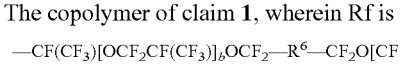

wherein
   $R^6$ is a perfluoroalkylene group; and
   b and d are integers with a sum in the range of 0 to 35.

3. A copolymer comprising at least one group of Formula (IV)

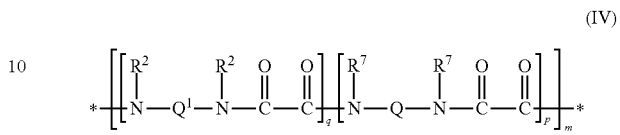

wherein
   $Q^1$ comprises a perfluoropolyether segment, wherein Q1 is of Formula (X) or (XI)

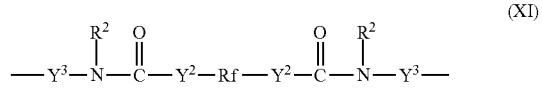

each $Y^1$ is independently (a) a heteroalkylene having at least two carbon atoms, (b) alkylene having at least two carbon atoms, or (c) a carbonylamino group linking a first group to a second group, wherein the first group and the second group are each a heteroalkylene having at least two carbon atoms or alkylene having at least two carbon atoms, or (d) a combination thereof;
   each $Y^2$ is independently a single bond, heteroalkylene having at least two carbon atoms, alkylene having at least two carbon atoms, or combination thereof; and
   each $Y^3$ is independently a heteroalkylene having at least two carbon atoms, alkylene having at least two carbon atoms, or combination thereof; and
   Rf is a perfluoropolyether group;
   Q is (a) a heteroalkylene, (b) alkylene, (c) arylene, (d) a carbonylamino group linking a first group to a second group, where each first group and second group is independently a heteroalkylene, alkylene, arylene, or a combination thereof, (e) part of a heterocyclic group that includes $R^7$ and the nitrogen to which $R^7$ is attached, or (f) a combination thereof; and
   each $R^2$ is independently hydrogen, alkyl, aralkyl, or aryl;
   each $R^7$ is independently hydrogen, alkyl, aralkyl, aryl, or a part of a heterocyclic group that includes Q and the nitrogen to which $R^7$ is attached;
   each variable q, p, and m is independently an integer equal to at least 1; and
   each asterisk denotes a site of attachment to another group in the copolymer.

4. The copolymer of claim 3, wherein Rf is of formula

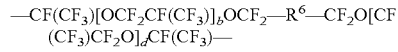

wherein
   $R^6$ is a perfluoroalkylene group; and
   b and d are integers with a sum in the range of 0 to 35.

5. The copolymer of claim 3, wherein at least one of p or q is equal to 1.

* * * * *

UNITED STATES PATENT AND TRADEMARK OFFICE
CERTIFICATE OF CORRECTION

PATENT NO. : 8,907,046 B2  
APPLICATION NO. : 13/514661  
DATED : December 9, 2014  
INVENTOR(S) : Suresh Iyer Page 1 of 1

It is certified that error appears in the above-identified patent and that said Letters Patent is hereby corrected as shown below:

In the Specification

Column 7
Line 43, delete "polyl" and insert -- poly --, therefor.

Column 14
Line 39, delete "piperizine." and insert -- piperazine. --, therefor.

Line 53, delete "polyoxypropropylene" and insert -- polyoxypropylene --, therefor.

Column 15
Lines 14-15 (Approx.), delete "isophorene" and insert -- isophorone --, therefor.

Column 20
Line 30 (Approx.), delete "piperizine." and insert -- piperazine. --, therefor.

In the Claims

Column 34
Line 16 (Approx.), in Claim 3, delete "Q1" and insert -- $Q^1$ --, therefor.

Signed and Sealed this  
Twenty-eighth Day of July, 2015

Michelle K. Lee  
*Director of the United States Patent and Trademark Office*